US012600755B2

(12) United States Patent
Li et al.

(10) Patent No.: US 12,600,755 B2
(45) Date of Patent: Apr. 14, 2026

(54) COBRA 1/NELF-B AS A BOOSTER FOR EFFICACY OF CD8+ T CELL-BASED THERAPY

(71) Applicant: The George Washington University, A Congressionally Chartered Not-for-Profit Corporation, Washington, DC (US)

(72) Inventors: Rong Li, Washington, DC (US); Bogang Wu, Washington, DC (US)

(73) Assignee: The George Washington University, A Congressionally Chartered Not-for-Profit Corporation, Washington, DC (US)

( * ) Notice: Subject to any disclaimer, the term of this patent is extended or adjusted under 35 U.S.C. 154(b) by 784 days.

(21) Appl. No.: 17/905,134

(22) PCT Filed: Feb. 25, 2021

(86) PCT No.: PCT/US2021/019688
§ 371 (c)(1),
(2) Date: Aug. 26, 2022

(87) PCT Pub. No.: WO2021/173847
PCT Pub. Date: Sep. 2, 2021

(65) Prior Publication Data
US 2023/0104519 A1 Apr. 6, 2023

Related U.S. Application Data

(60) Provisional application No. 62/982,514, filed on Feb. 27, 2020.

(51) Int. Cl.
*C07K 14/47* (2006.01)
*A61K 40/11* (2025.01)
(Continued)

(52) U.S. Cl.
CPC .......... *C07K 14/4702* (2013.01); *A61K 40/11* (2025.01); *A61K 40/31* (2025.01);
(Continued)

(58) Field of Classification Search
CPC .... C07K 14/4702; A61K 40/11; A61K 40/31; A61K 40/4211; A61K 2239/31;
(Continued)

(56) References Cited

U.S. PATENT DOCUMENTS

2007/0031848 A1 2/2007 Cargill et al.
2010/0190656 A1 7/2010 Li et al.
(Continued)

FOREIGN PATENT DOCUMENTS

WO WO-200153312 A1 7/2001
WO WO-2004003190 A1 1/2004
WO WO-2017161092 A1 9/2017

OTHER PUBLICATIONS

Yu, L., Zhang, B., Deochand, D. et al. Negative elongation factor complex enables macrophage inflammatory responses by controlling anti-inflammatory gene expression. Nat Commun 11, 2286 (2020) (Year: 2020).*
(Continued)

*Primary Examiner* — Tracy Vivlemore
*Assistant Examiner* — Thomas R. Amick
(74) *Attorney, Agent, or Firm* — Kory D. Christensen

(57) ABSTRACT

The present disclosure provides a method of generating a T cell comprising a transgene integrated at a first site within the genome of the T cell, wherein the transgene encodes a polypeptide that is a subunit of a negative elongation factor (NELF) complex. The T cells can be administered to treat cancer and infectious disease.

19 Claims, 24 Drawing Sheets

Figure 1:
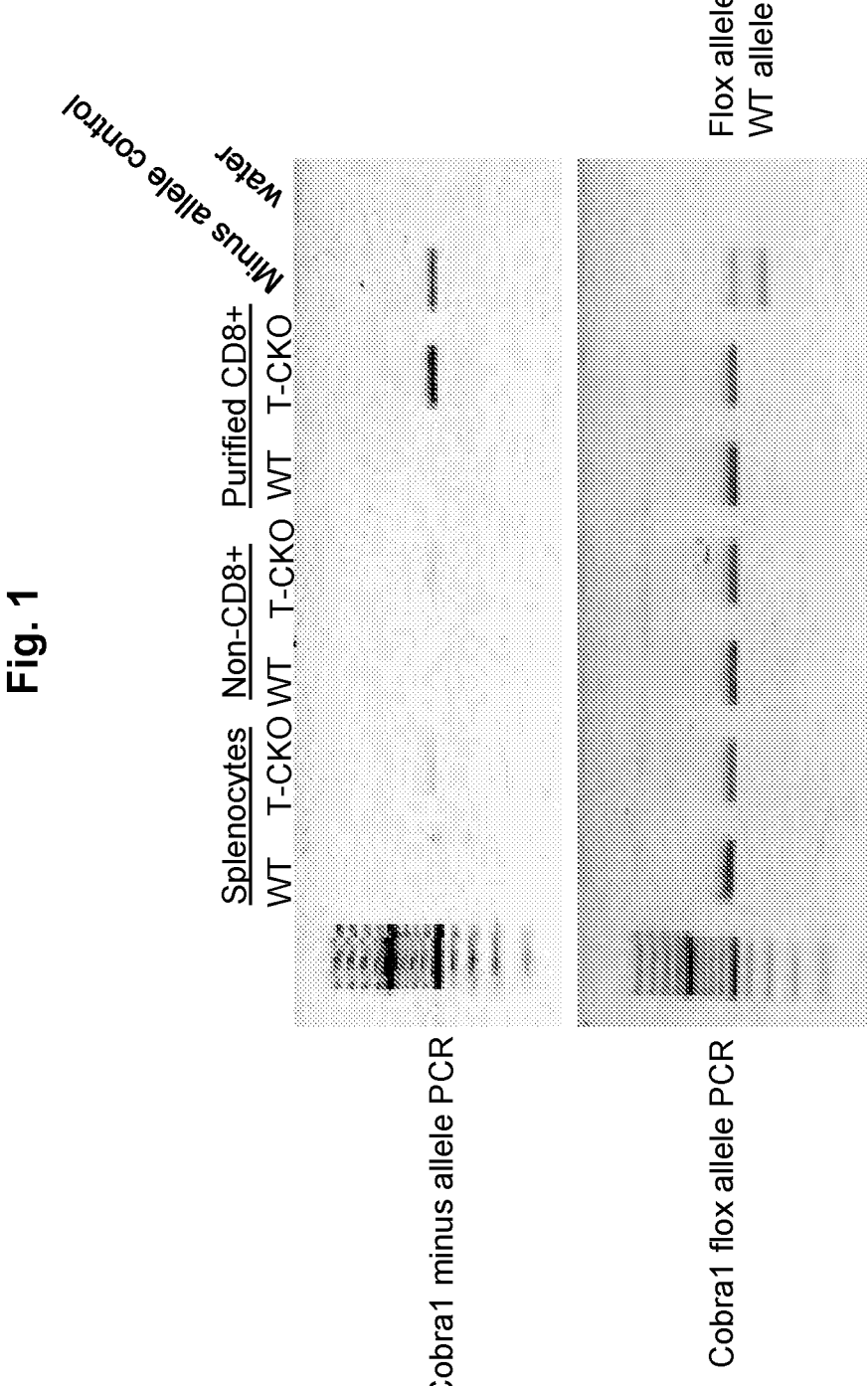

Specification includes a Sequence Listing.

Cobra1 minus allele PCR

Splenocytes  Non-CD8+  Purified CD8+  Minus allele control  water
WT   T-CKO WT   T-CKO  WT   T-CKO Cobra1 flox allele PCR Flox allele
WT allele

(51) Int. Cl.

| | |
|---|---|
| *A61K 40/31* | (2025.01) |
| *A61K 40/42* | (2025.01) |
| *A61P 35/00* | (2006.01) |
| *C12N 5/0783* | (2010.01) |

(52) U.S. Cl.
 CPC .......... *A61K 40/4211* (2025.01); *A61P 35/00* (2018.01); *C12N 5/0636* (2013.01); *A61K 2239/31* (2023.05); *A61K 2239/57* (2023.05)

(58) Field of Classification Search
 CPC .... A61K 2239/57; A61K 48/00; A61K 38/00; A61P 35/00; C12N 5/0636; C12N 2740/16043; C12N 2510/00; A01K 2207/12; A01K 2217/052; A01K 2217/075; A01K 2217/206; A01K 2227/105
 See application file for complete search history.

(56) References Cited

U.S. PATENT DOCUMENTS

| | | |
|---|---|---|
| 2016/0237429 A1 | 8/2016 | Cubillos-Ruiz et al. |
| 2019/0192691 A1 | 6/2019 | Barrett et al. |

OTHER PUBLICATIONS

Chen, Z., et al., "TCF-1-Centered Transcriptional Network Drives an Effector versus Exhausted CD8 T Cell-Fate Decision," Immunity 51(5):840-855, Cell Press, United States (Nov. 2019).

Wang, Y., et al., "The Transcription Factor TCF1 Preserves the Effector Function of Exhausted CD8 T Cells During Chronic Viral Infection," Front Immunol 10:169, Frontiers Media S.A., Switzerland (Feb. 2019).

Kaech, S., and Cui, W., "Transcriptional control of effector and memory CD8+ T cell differentiation," Nat Rev Immunol 12(11):749-761, Nature Publishing Group, United Kingdom (Nov. 2012).

Wu, B., et al., "RNA polymerase II pausing factor NELF in CD8+ T cells promotes antitumor immunity," Nat Commun 13(1):2155, Nature Publishing Group, United Kingdom (Apr. 2022).

International Search Report and Written Opinion for International Application No. PCT/US2021/019688, mailed Jun. 25, 2021, International Searching Authority, United States, 14 pages.

Ishii, A., et al., "Analysis of the role of homology arms in gene-targeting vectors in human cells," Plos One 9:e108236, Plos, United States (2014).

Natarajan, M., et al., "Negative elongation factor (NELF) coordinates RNA polymerase II pausing, premature termination, and chromatin remodeling to regulate HIV transcription," J. Biol. Chem. 288:25995-26003, Elsevier, Netherlands (2013).

* cited by examiner

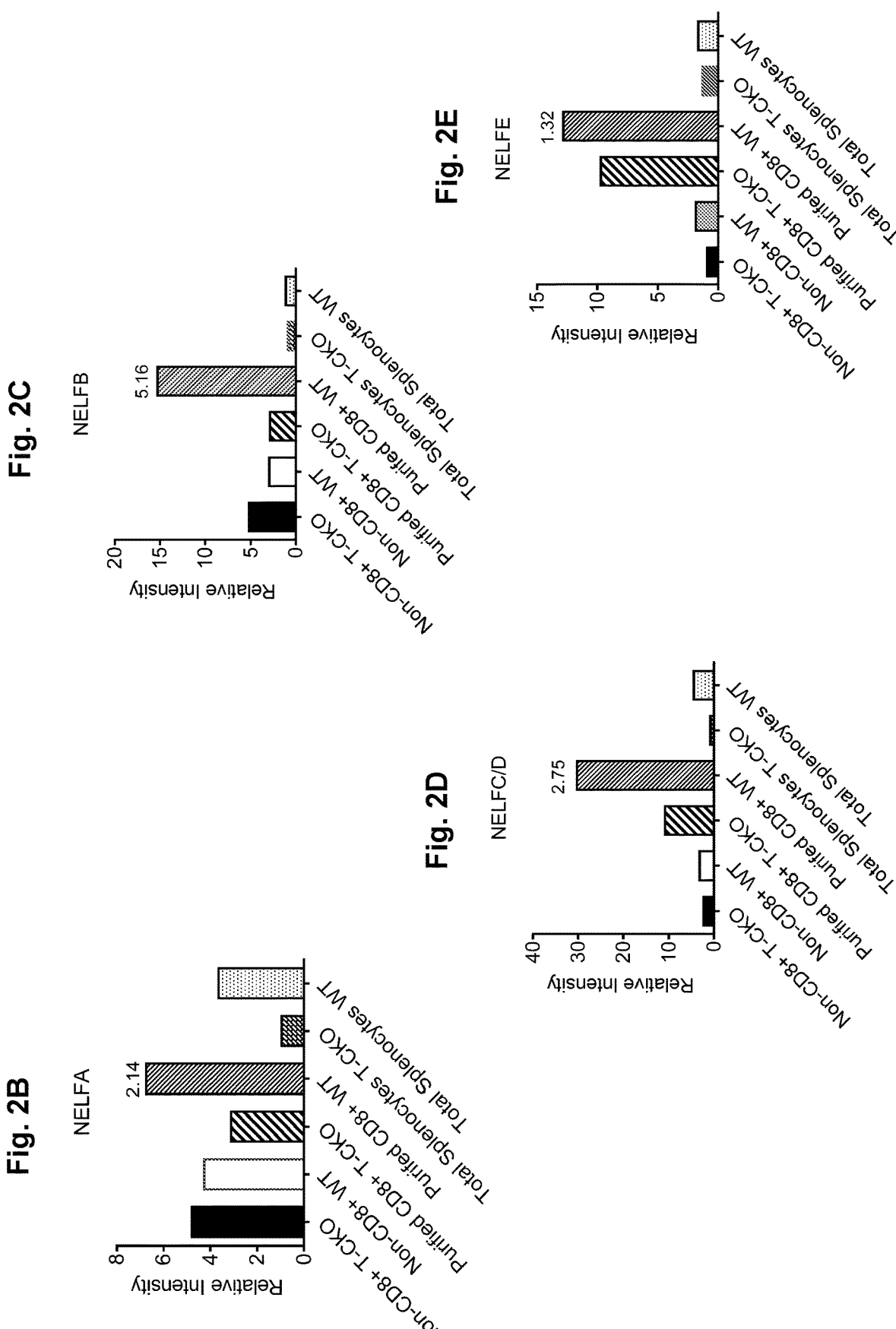

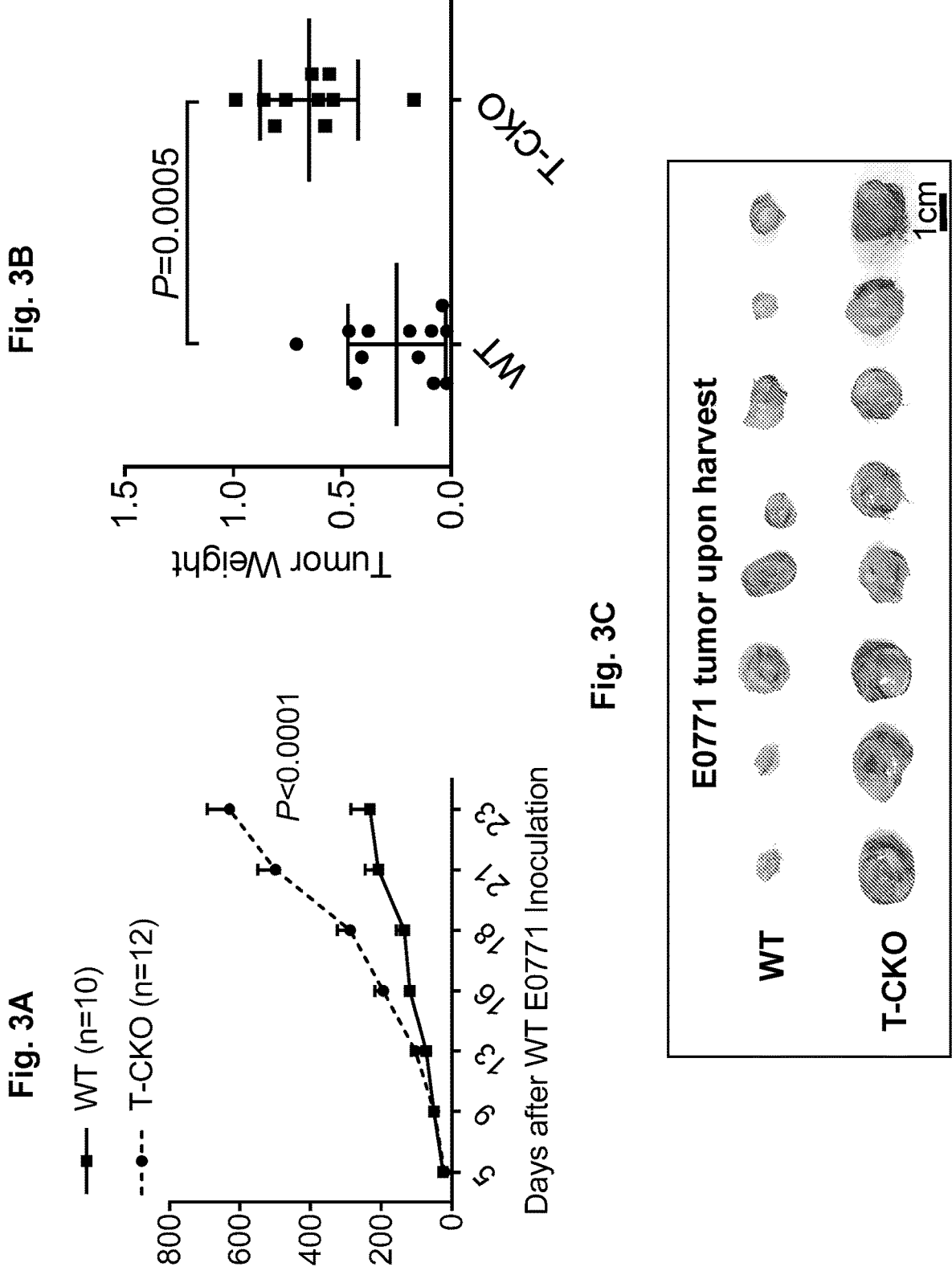

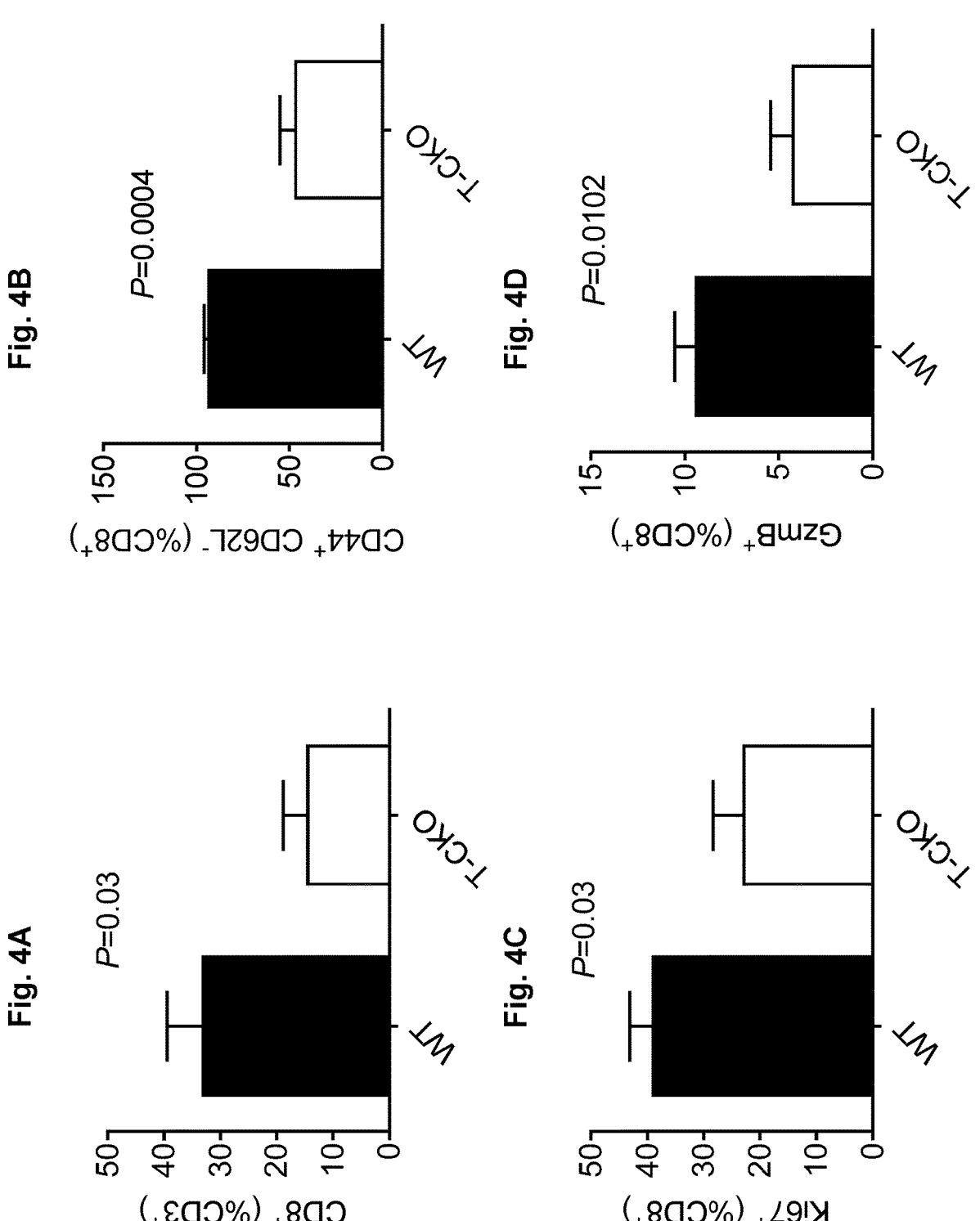

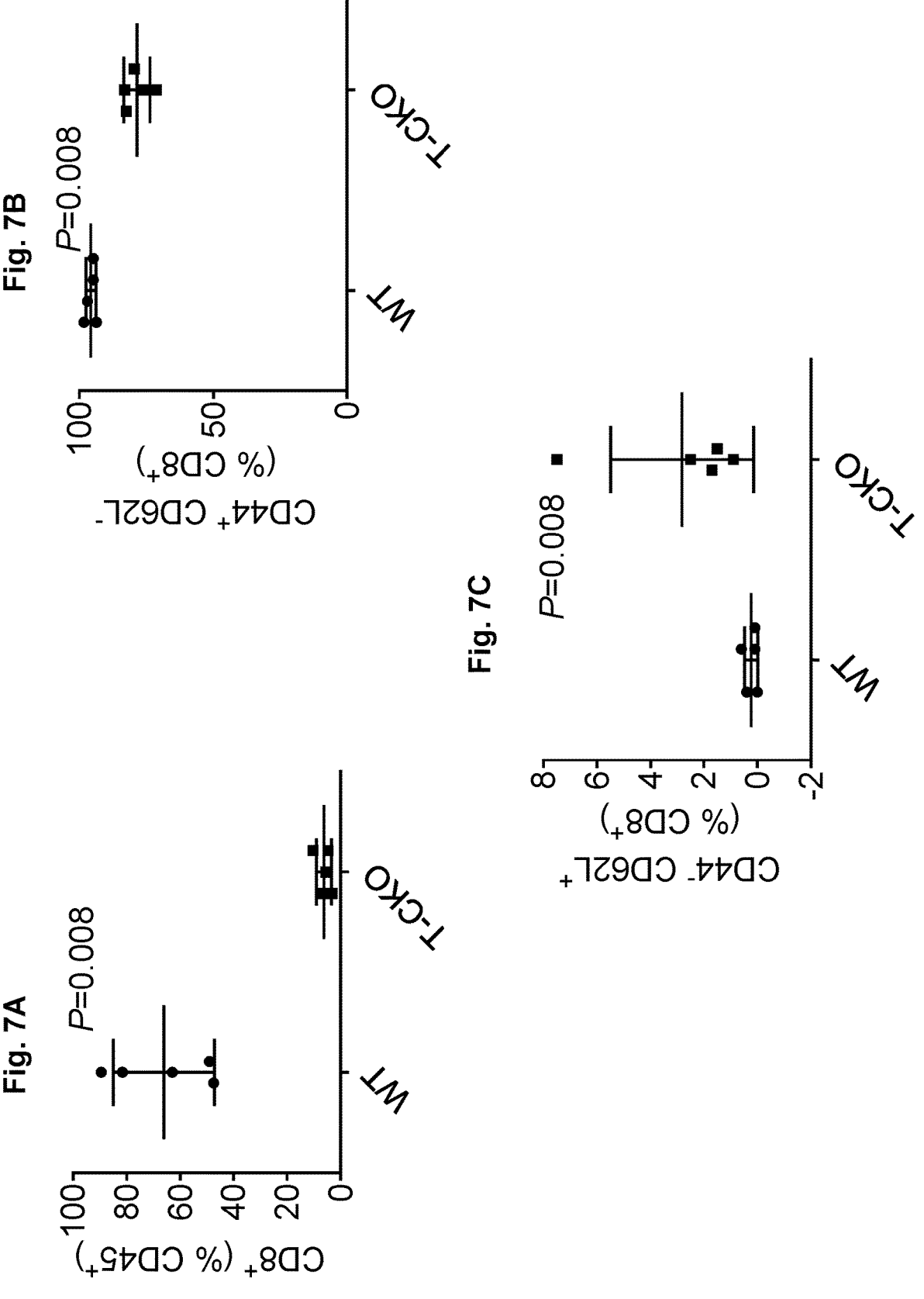

Male

Female

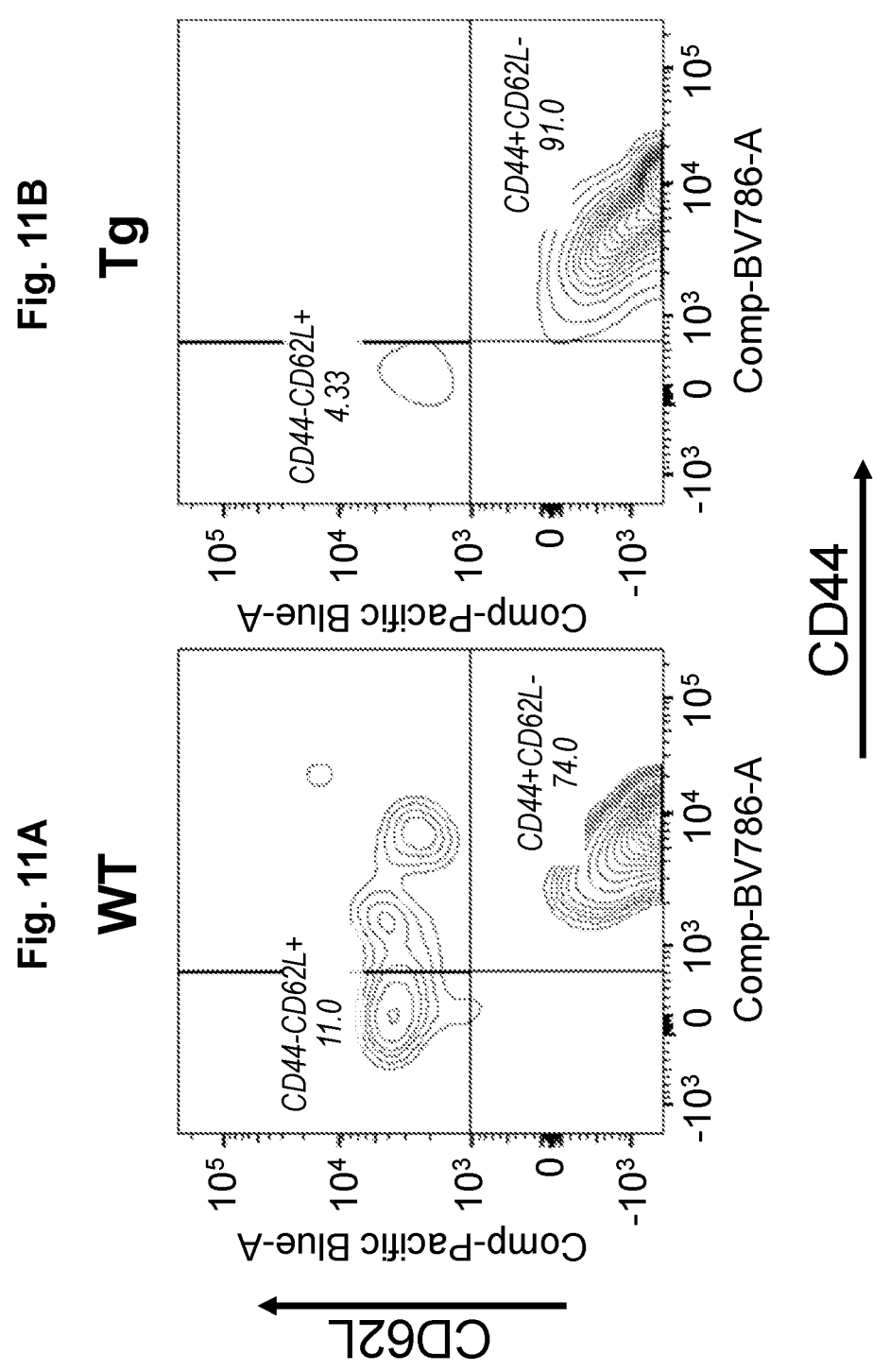

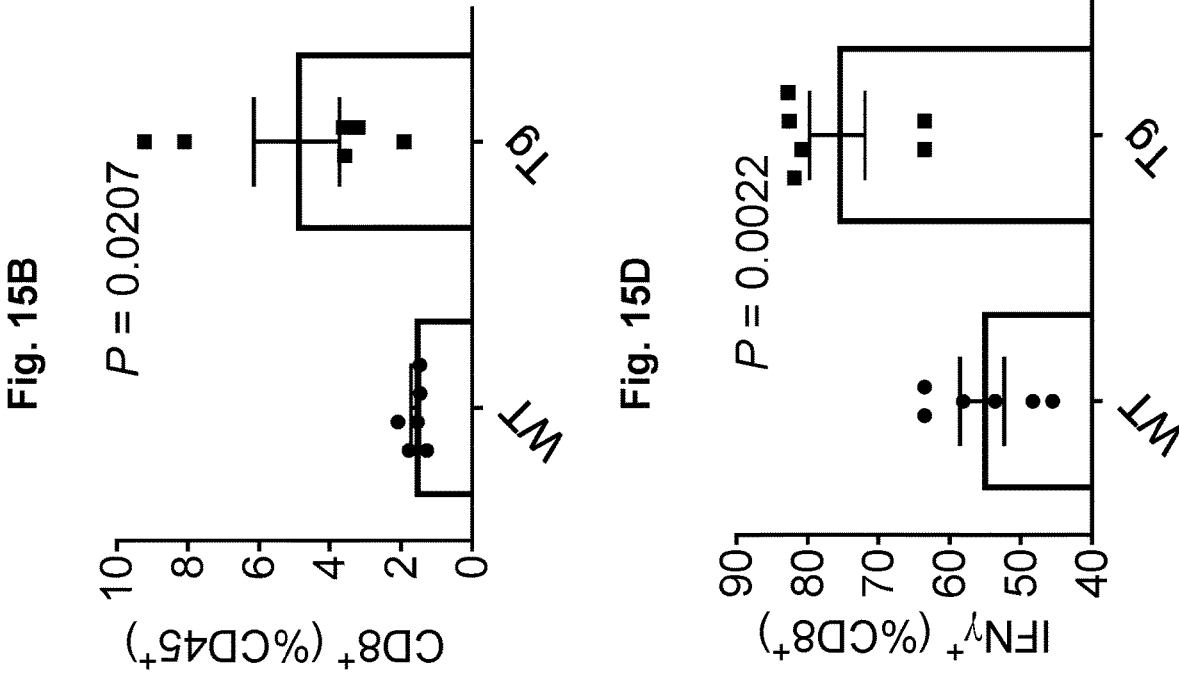
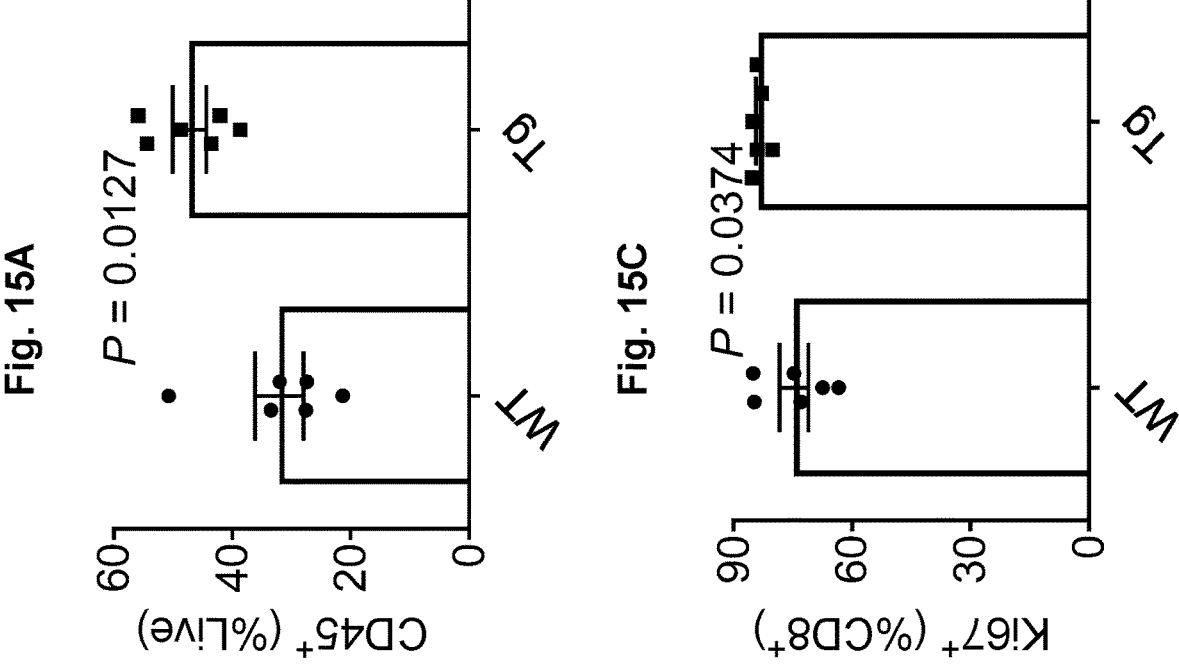

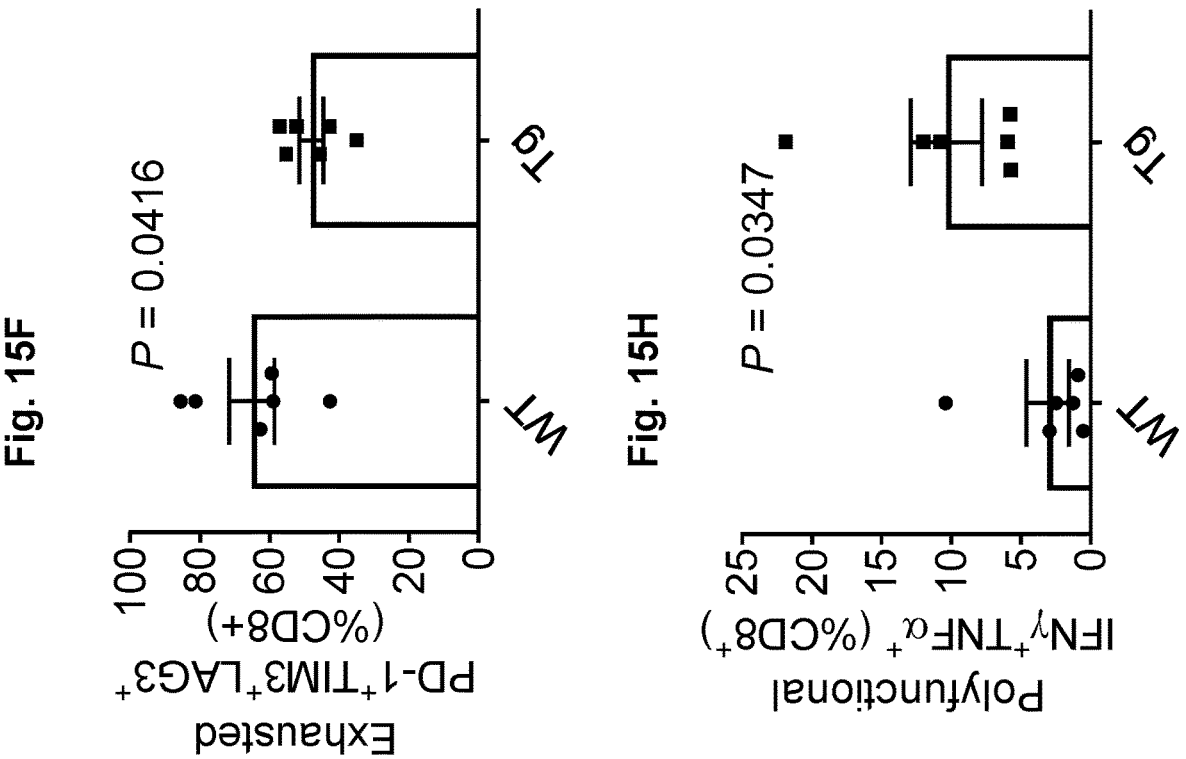
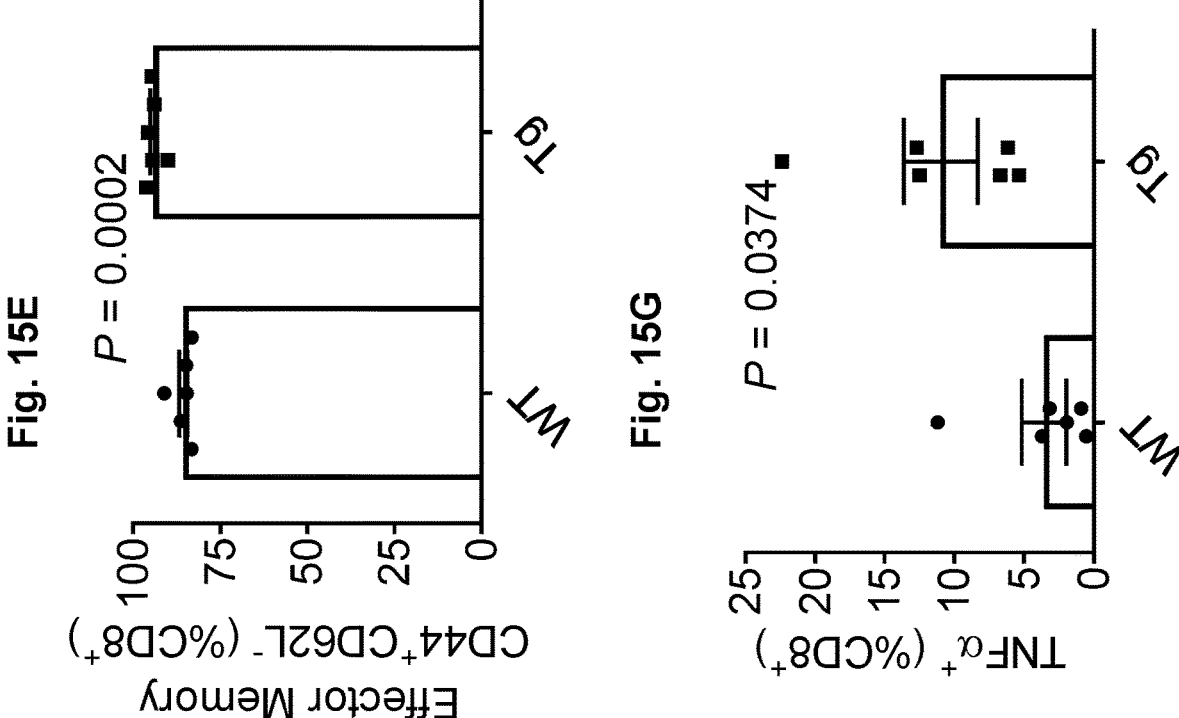

COBRA 1/NELF-B AS A BOOSTER FOR EFFICACY OF CD8+ T CELL-BASED THERAPY

CROSS REFERENCE TO RELATED APPLICATIONS

This application claims the benefit of U.S. Provisional Application No. 62/982,514, filed Feb. 27, 2020, which is hereby incorporated by reference in its entirety.

REFERENCE TO SEQUENCE LISTING SUBMITTED ELECTRONICALLY

The content of the electronically submitted sequence listing in ASCII text file (Name: 3973_015PC01_Seqlisting_ST25; Size: 35,374 bytes; and Date of Creation: Feb. 11, 2021) filed with the application is incorporated herein by reference in its entirety.

BACKGROUND OF THE INVENTION

Field of the Invention

The present disclosure provides T cells comprising a transgene integrated at a first site within the genome of the T cell, wherein the transgene encodes a polypeptide that is a subunit of a NELF complex and methods of using the same.

Background

Negative elongation factor (NELF) is a complex comprising the subunits NELF-A, NELF-B, NELF-C or NELF-D, and NELF-E. NELF-C and NELF-D are produced from alternative translation initiation sites in the same RNA resulting in isoforms with different N-termini. Cofactor of BRCA1 (COBRA1), also known as Negative Elongation Factor B (NELF-B), is involved in regulation of RNA polymerase II pausing and gene transcription.

Existing T cell therapy does not work effectively in the treatment of solid tumors, partly due to T cell exhaustion and lack of sufficient memory T cell populations to deliver anti-tumor cytotoxicity in a durable fashion. Thus, new therapies are needed to solve this problem.

BRIEF SUMMARY OF THE INVENTION

In one aspect, the present disclosure provides a T cell comprising a transgene integrated at a first site within the genome of the T cell, wherein the transgene encodes a polypeptide that is a subunit of a negative elongation factor (NELF) complex.

In one aspect, the present disclosure provides a T cell comprising a transgene integrated at a first site within the genome of the T cell, wherein the transgene encodes a polypeptide that is COBRA1.

In another aspect, the present disclosure provides a method of treating a cancer in a subject in need thereof, comprising administering to the subject a therapeutically effective amount of a T cell or population of T cells, wherein the T cell or population of T cells comprise a transgene integrated at a first site within the genome of the T cell, wherein the transgene encodes a polypeptide that is a subunit of a NELF complex.

In another aspect, the present disclosure provides a method of treating a cancer in a subject in need thereof, comprising administering to the subject a therapeutically effective amount of a T cell or population of T cells, wherein the T cell or population of T cells comprise a transgene integrated at a first site within the genome of the T cell, wherein the transgene encodes a polypeptide that is COBRA1.

In another aspect, the present disclosure provides a method of generating a T cell comprising: introducing into a T cell (i) a transgene, and (ii) a homologous recombination system suitable for targeted integration of the transgene at a site within the genome of the cell, whereby the homologous recombination system integrates the transgene at said site within the genome of the cell, and wherein expression of the transgene is increased relative to the endogenous expression level, wherein the transgene encodes a polypeptide that is a subunit of a NELF complex.

In another aspect, the present disclosure provides a method of generating a T cell comprising: introducing into a T cell (i) a transgene, and (ii) a homologous recombination system suitable for targeted integration of the transgene at a site within the genome of the cell, whereby the homologous recombination system integrates the transgene at said site within the genome of the cell, and wherein expression of the transgene is increased relative to the endogenous expression level, wherein the transgene encodes a polypeptide that is COBRA1.

In another aspect, the present disclosure provides a composition comprising a population of isolated T cells modified to overexpress one or more of a subunit of a NELF complex.

In another aspect, the present disclosure provides a composition comprising a population of isolated T cells modified to overexpress COBRA1.

In another aspect, the present disclosure provides a method of enhancing a T cell immune response against cancer or infectious disease comprising overexpressing COBRA1 in the T cell.

BRIEF DESCRIPTION OF THE DRAWINGS/FIGURES

FIG. 1 is a DNA gel showing PCR amplification of a COBRA1 deleted allele (Cobra1 minus allele), Cobra1 floxed allele (Cobra1 fox allele), and WT Cobra1 allele. T-CKO: T cell-specific Cobra1 knockout; WT: wildtype.

Figure 2A:
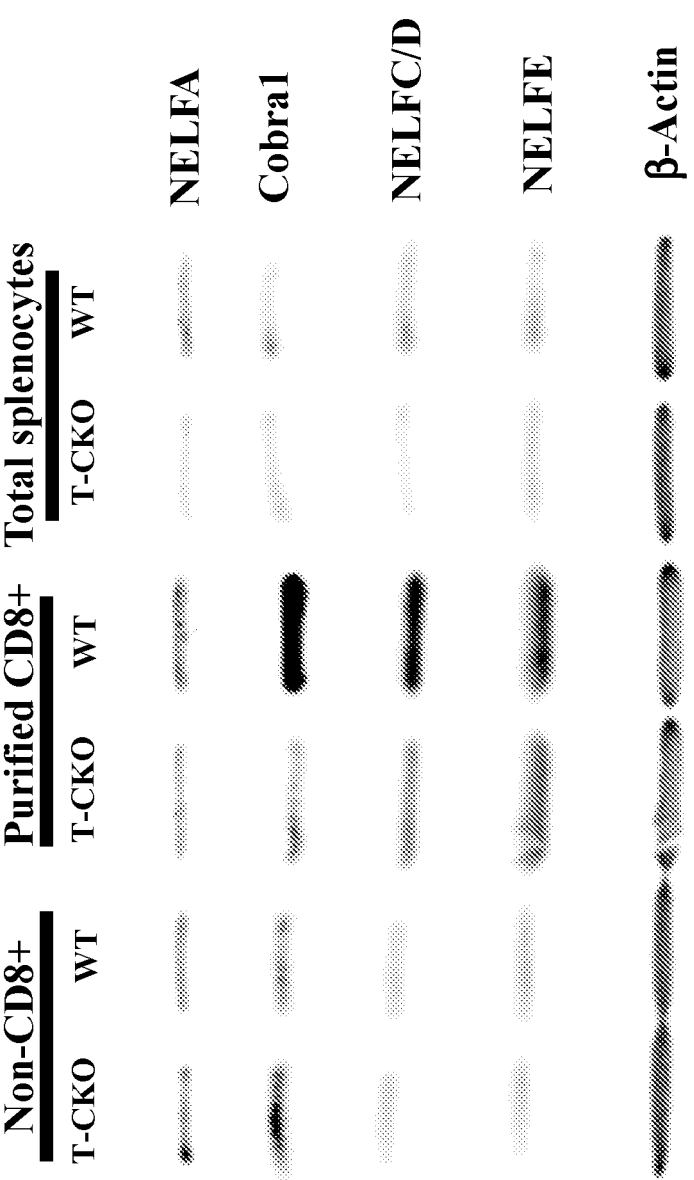

FIG. 2 shows the T cell specific knockout of Cobra1 in mice. FIG. 2A is a western blot showing expression of NELFA, Cobra1, NELFC/D, NELFE, and ($\beta$-actin in cell harvested from WT or Cobra1 knockout mice. FIG. 2B is a bar graph showing the quantification of NEFLA expression in WT or Cobra1 knockout. FIG. 2C is a bar graph showing the quantification of NELFB expression in WT or Cobra1 knockout. FIG. 2D is a bar graph showing the quantification of NELFC/D expression in WT or Cobra1 knockout. FIG. 2E is a bar graph showing the quantification of NELFE expression in WT or Cobra1 knockout. The value given is the fold change of protein expression in WT CD8+ T cells compared to T-CKO CD8+ T cells. T-CKO: T cell specific knockout of Cobra1; WT: wildtype.

FIG. 3 shows the growth of mouse mammary tumor cells (E0771) in WT or T cell specific Cobra1 knockout mice. FIG. 3A is a graph showing the quantification of tumor volume in WT or Cobra1 knockout mice. FIG. 3B is a graph showing the quantification of tumor weight in WT or Cobra1 knockout mice. FIG. 3C is a photograph of tumors harvested from WT or Cobra1 knockout mice. T-CKO: T cell specific Cobra1 knockout; WT: wildtype.

FIG. 4 shows the number of tumor-infiltrating cells in WT or T cell specific Cobra1 knockout mice. FIG. 4A is a bar graph showing the percentage of CD3+ cells that are CD8+ in WT or Cobra1 knockout mice. FIG. 4B is a bar graph showing the percentage of CD8+ cells that are CD44+ CD62L− in WT or Cobra1 knockout mice. FIG. 4C is a bar graph showing the percentage of CD8+ cells that are Ki67+ in WT or Cobra1 knockout mice. FIG. 4D is a bar graph showing the percentage of CD8+ cells that are GzmB+ in WT or Cobra1 knockout mice. T-CKO: T cell specific Cobra1 knockout; WT: wildtype.

Figure 5B:
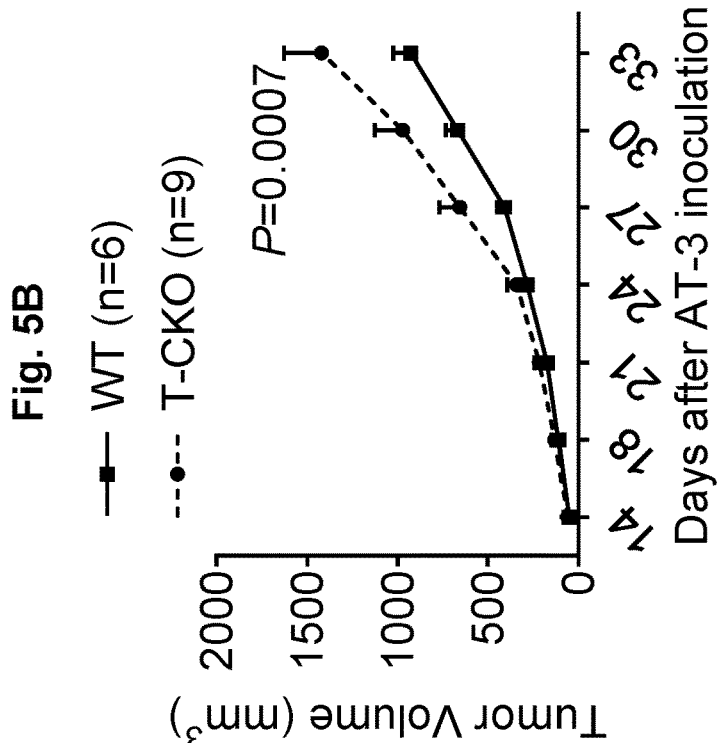
Figure 5A:
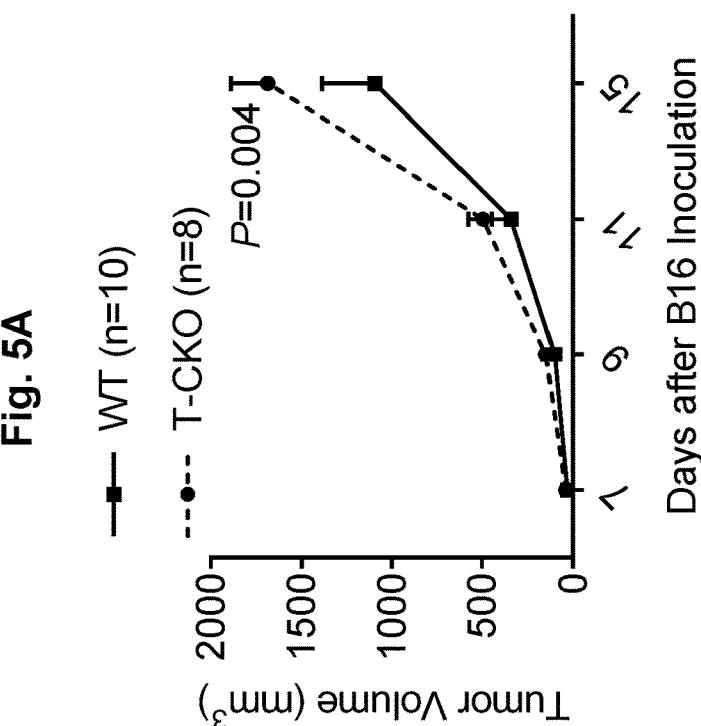

FIG. 5 shows the growth of B16 melanoma cells or AT-3 mammary tumor cells in WT or T cell specific Cobra1 knockout mice. FIG. 5A is a graph showing the quantification of B16 tumor volume in WT or Cobra1 knockout mice. FIG. 5B is a graph showing the quantification of AT-3 tumor volume in WT or Cobra1 knockout mice. T-CKO: Cobra1 knockout; WT: wildtype.

Figure 6B:
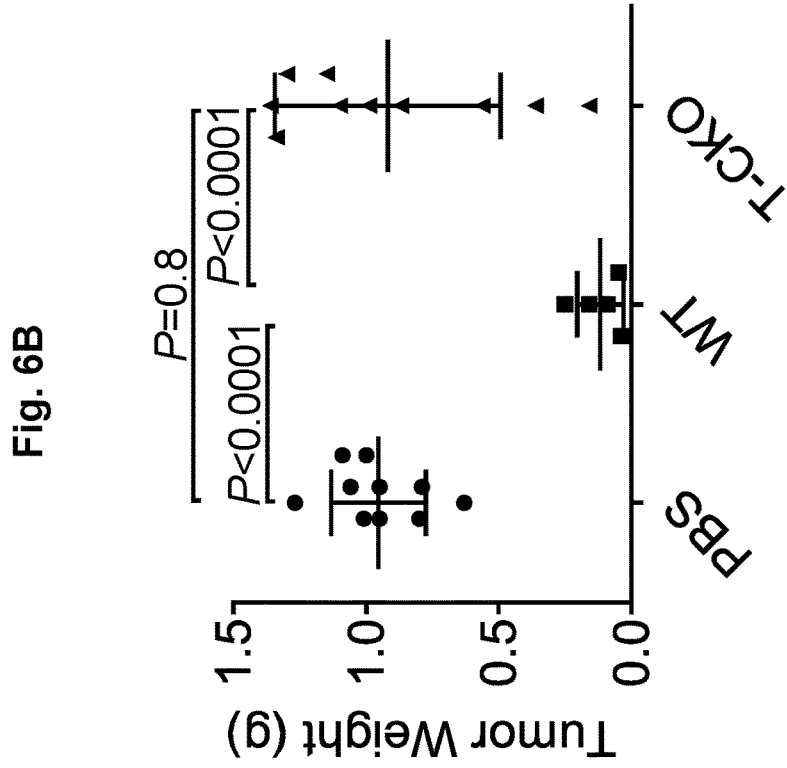
Figure 6A:
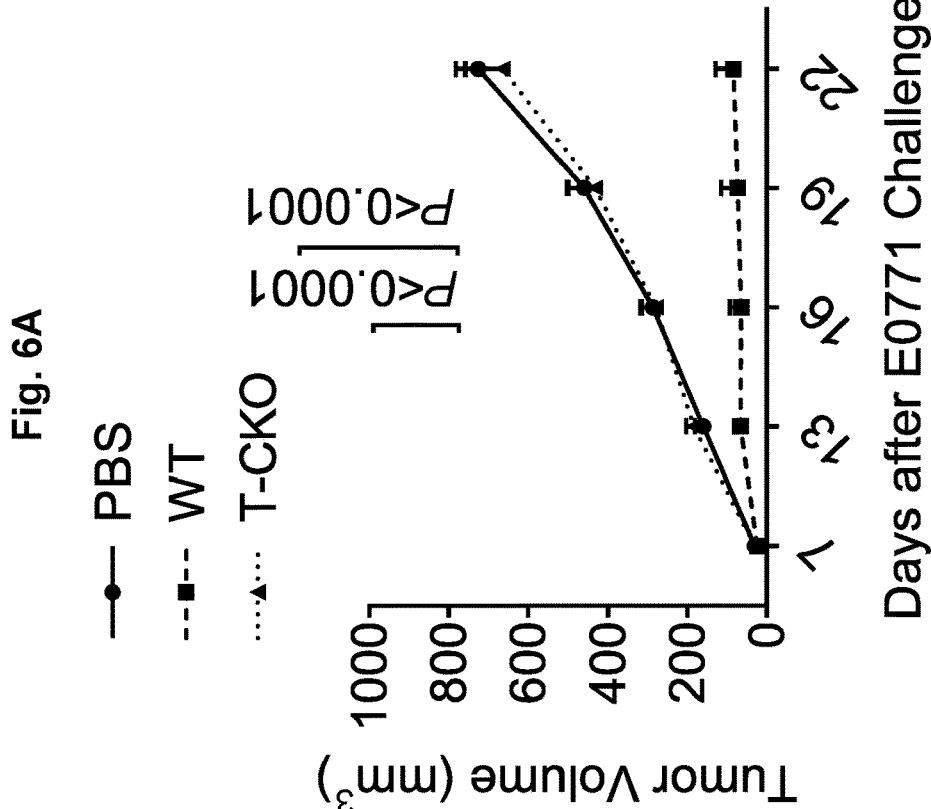

FIG. 6 shows the growth of mouse mammary tumor cells (E0771) in Rag1−/− immunodeficient mice after transfer of purified WT or T cell specific Cobra1 knockout CD8+ T cells. FIG. 6A is a bar graph showing the tumor volume of immunodeficient mice that were transferred WT CD8+ T cells, Cobra1 knockout CD8+ T cells, or a PBS control. FIG. 6B is a bar graph showing the tumor weight of immunodeficient mice that were transferred WT CD8+ T cells, Cobra1 knockout CD8+ T cells, or a PBS control. T-CKO: T cell specific Cobra1 knockout; WT: wildtype.

FIG. 7 shows the number of tumor-infiltrating cells in Rag1−/− immunodeficient mice that were transferred with either purified WT CD8+ T cells or T cell specific Cobra1 knockout CD8+ T cells. FIG. 7A is a graph showing the percentage of CD45+ cells that are CD8+ in tumors isolated from Rag1−/− mice that were transferred with WT or Cobra1 knockout T cells. FIG. 7B is a graph showing the percentage of CD8+ T cells that are CD44+CD62L− in tumors isolated from Rag1−/− mice that were transferred with WT or Cobra1 knockout T cells. FIG. 7C is a graph showing the percentage of CD8+ T cells that are CD44-CD62L+ in tumors isolated from Rag1−/− mice that were transferred with WT or Cobra1 knockout T cells. T-CKO: T cell specific Cobra1 knockout; WT: wildtype.

Figure 8:
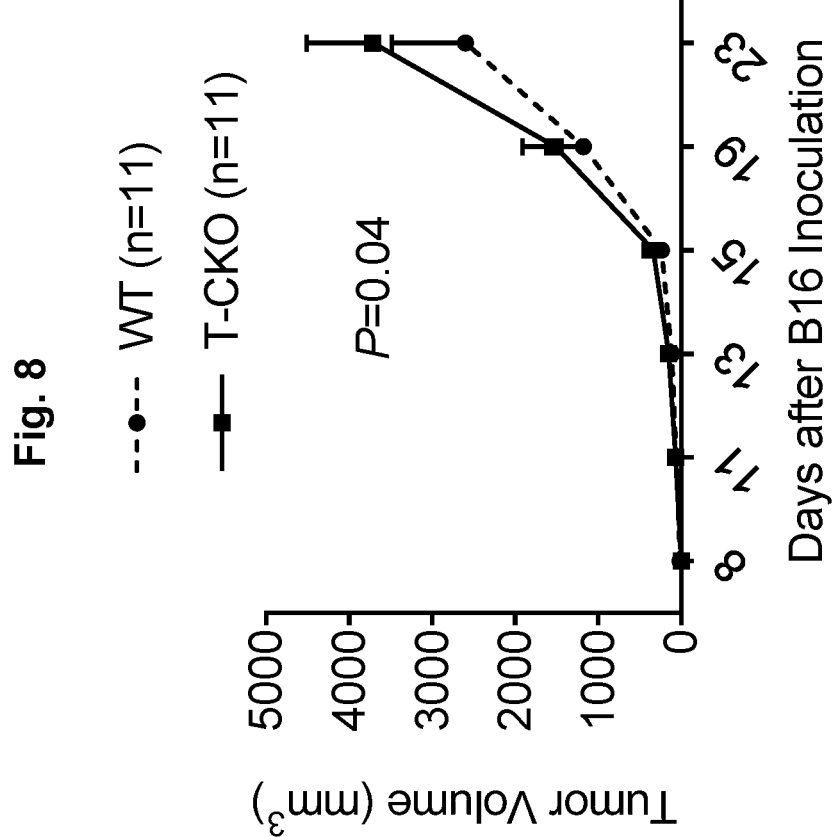

FIG. 8 shows the tumor volume of B16 melanoma cells in Rag1−/− immunodeficient mice after transfer of purified WT or T cell specific Cobra1 knockout CD8+ T cells. T-CKO: T cell specific Cobra1 knockout; WT: wildtype.

Figures 9A, 9B, 9C:
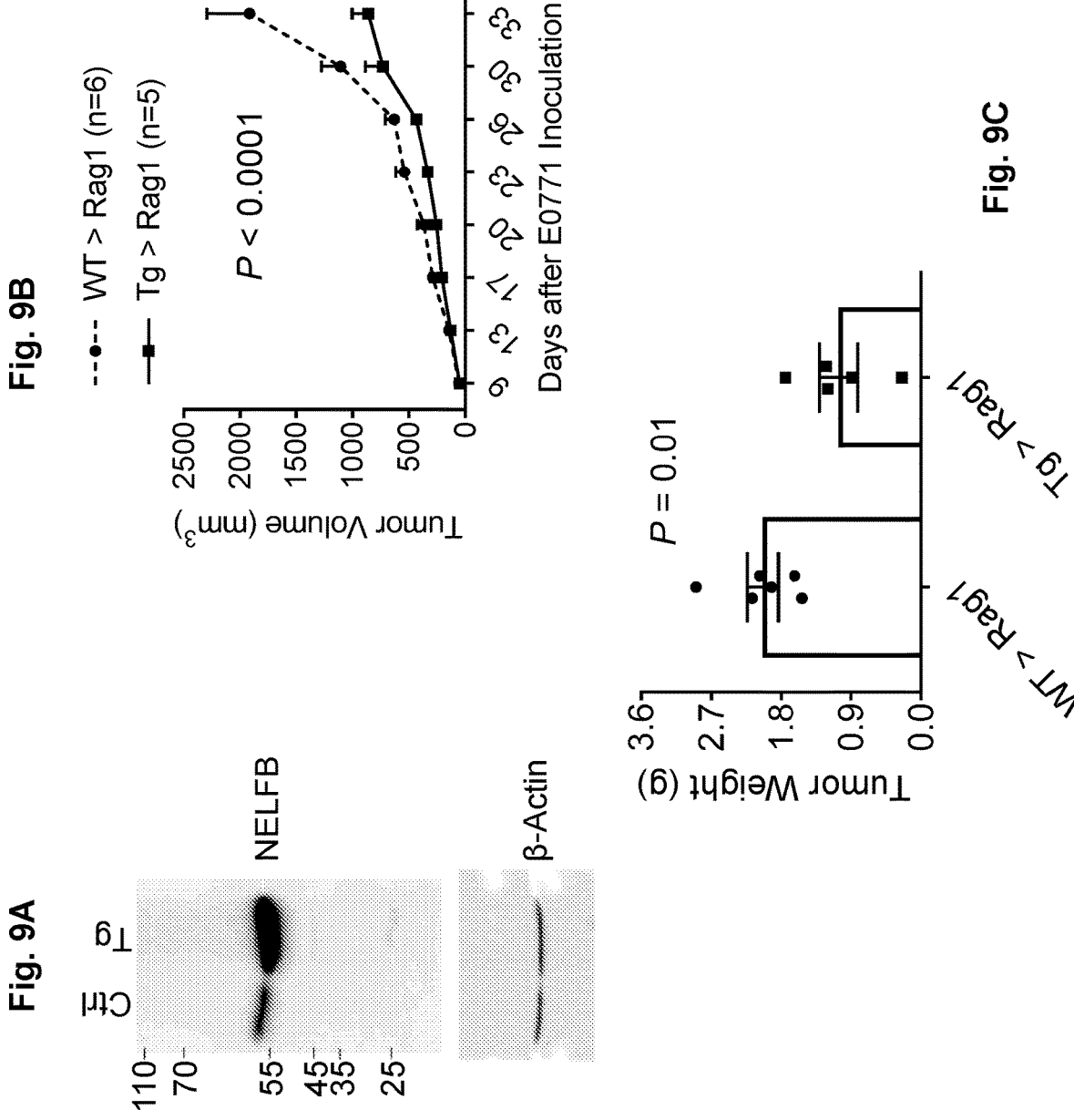
Figures 9D, 9E, 9F:
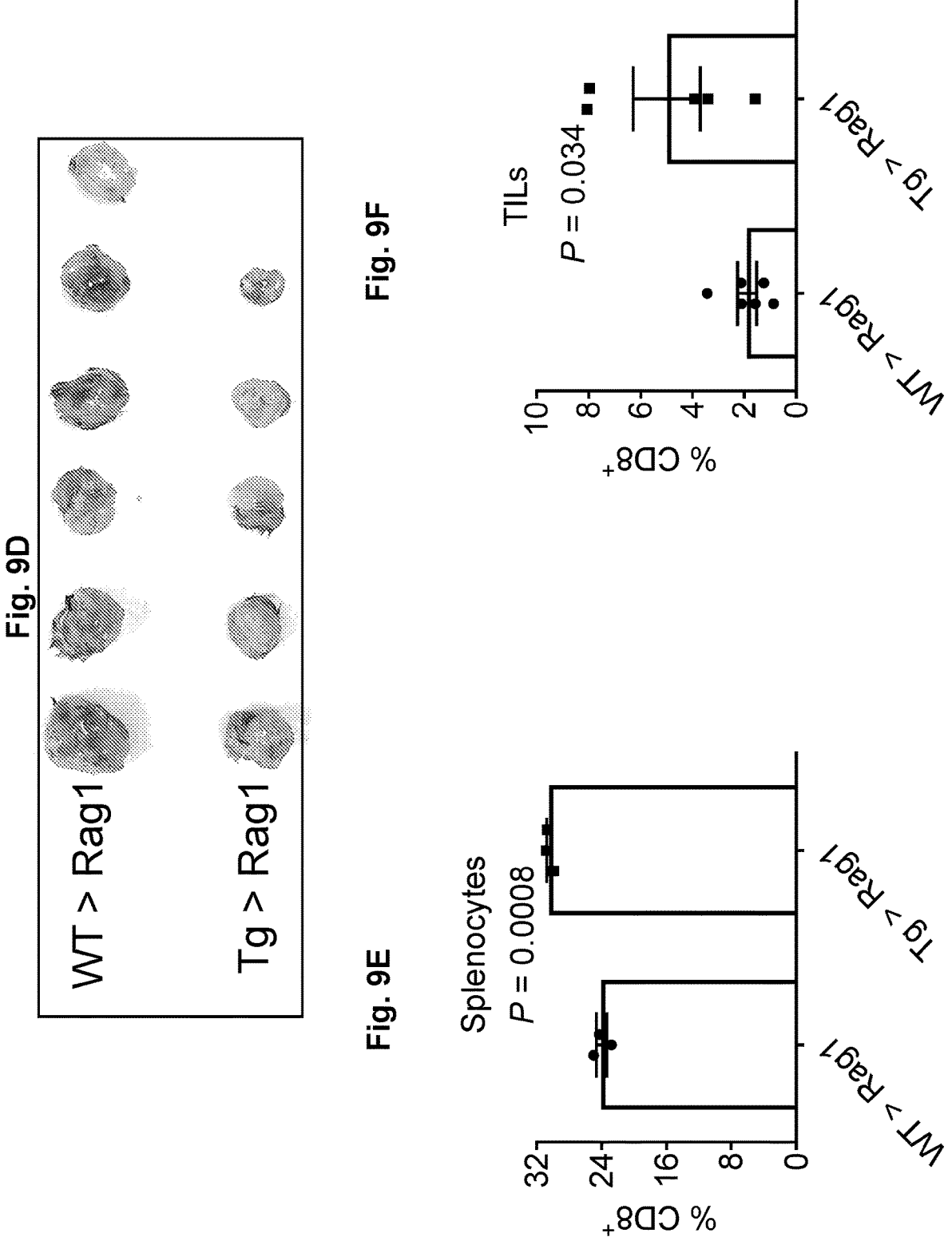

FIG. 9 shows the growth of mouse mammary tumor cells (E0771) in Rag1−/− immunodeficient mice after transfer of purified WT CD8+ T cells or Cobra1 transgene expressing T cells. FIG. 9A is a western blot showing expression of NELFB (Cobra1) in control or Cobra1 T cell specific transgenic mice splenocytes. FIG. 9B is a graph showing the tumor volume of Rag1−/− mice after transfer of WT or Cobra1 transgenic CD8+ T cells. FIG. 9C is a bar graph showing the tumor weight of Rag1−/− mice after transfer of WT or Cobra1 transgenic CD8+ T cells. FIG. 9D is a photograph of tumors harvested from Rag1−/− mice after transfer of WT or Cobra1 transgenic CD8+ T cells. FIG. 9E is a bar graph showing the percentage of CD8+ T cells isolated from the spleen in Rag1−/− mice after transfer of WT or Cobra1 transgenic CD8+ T cells. FIG. 9F is a bar graph showing the percentage of CD8+ tumor infiltrating lymphocytes from Rag1−/− mice after transfer of WT or Cobra1 transgenic CD8+ T cells. Tg: Cobra1 T cell specific transgene. TIL: tumor infiltrating lymphocyte.

Figure 10B:
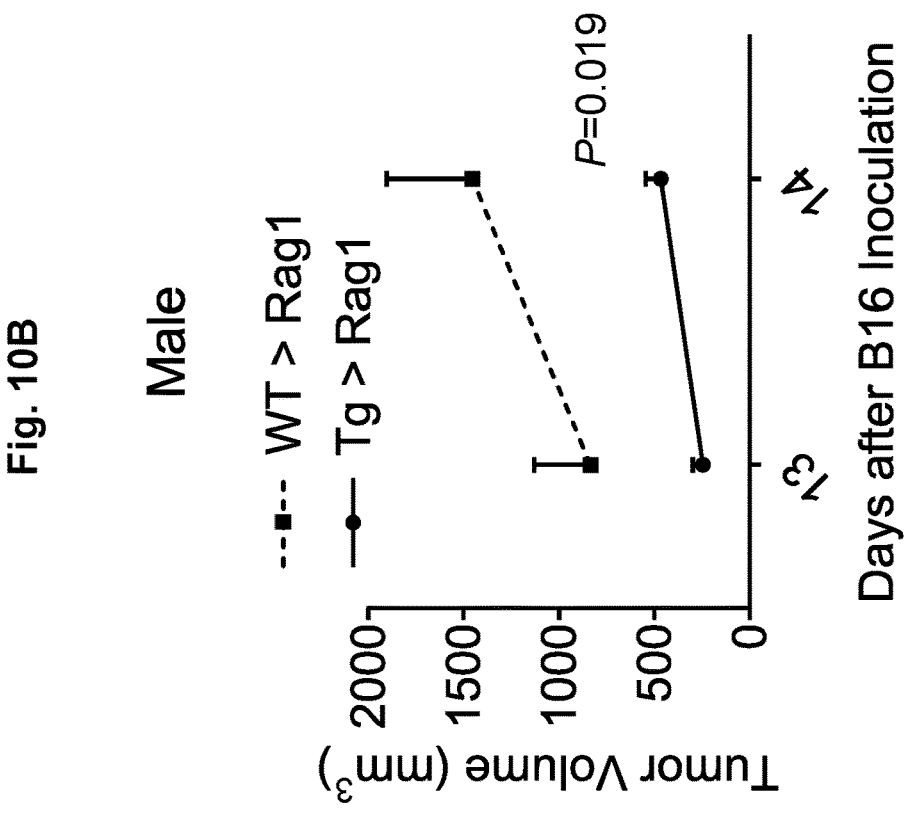
Figure 10A:
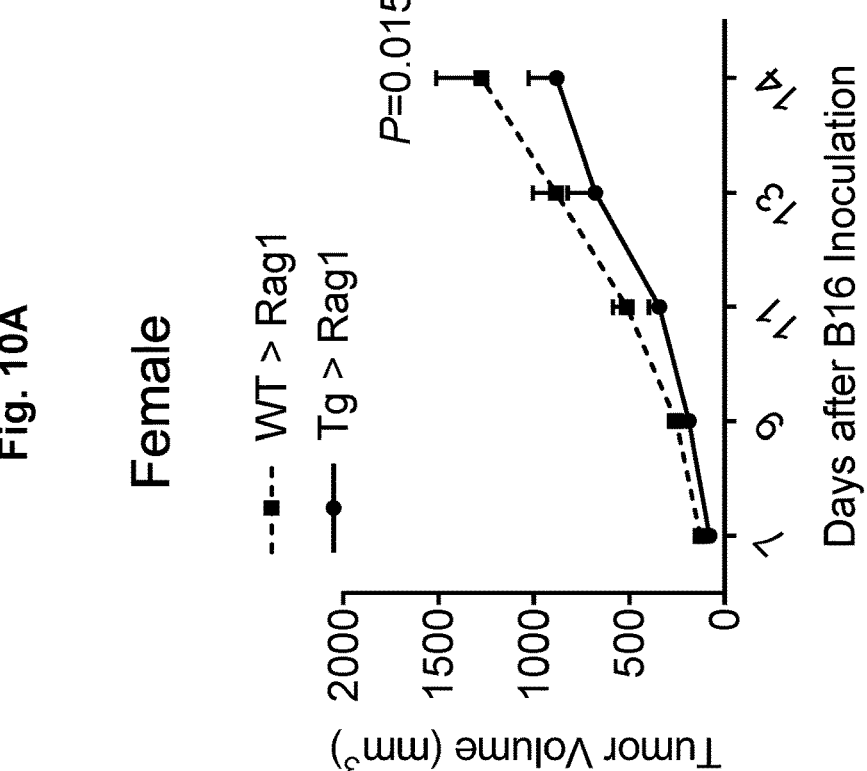

FIG. 10 shows the growth of B16 melanoma cells in male and female Rag1−/− immunodeficient mice after transfer of purified WT CD8+ T cells or Cobra1 transgene expressing T cells. FIG. 10A is a graph showing the tumor volume of Rag1−/− mice after transfer of WT CD8+ T cells or Cobra1 transgenic CD8+ T cells. FIG. 10B is a graph showing tumor volume of Rag1−/− mice after transfer of WT CD8+ T cells or Cobra1 transgenic CD8+ T cells. Tg: Cobra1 T cell specific transgene.

FIG. 11 shows the percent of effector memory and naïve CD8+ T cells in tumor bearing Rag1−/− mice after transfer of WT or Cobra1 transgenic CD8+ T cells. FIG. 11A is a flow cytometry plot showing the percent of CD44-CD62+ and CD44+CD62L− cells in tumor bearing Rag1−/− mice after transfer of WT CD8+ T cells. FIG. 11B is a flow cytometry plot showing the percent of CD44-CD62+ and CD44+CD62L− cells in tumor bearing Rag1−/− mice after transfer of Cobra1 transgene CD8+ T cells. Tg: Cobra1 T cell specific transgene.

FIG. 12 shows the percent of total tumor infiltrating CD8+ T cells that are wildtype, T-CKO (Cobra1 knockout), or Tg (Cobra 1 overexpression) after transfer of wildtype and T-CKO T cells or wildtype and Tg T cells into melanoma bearing Rag1−/− mice.

Figure 12A:
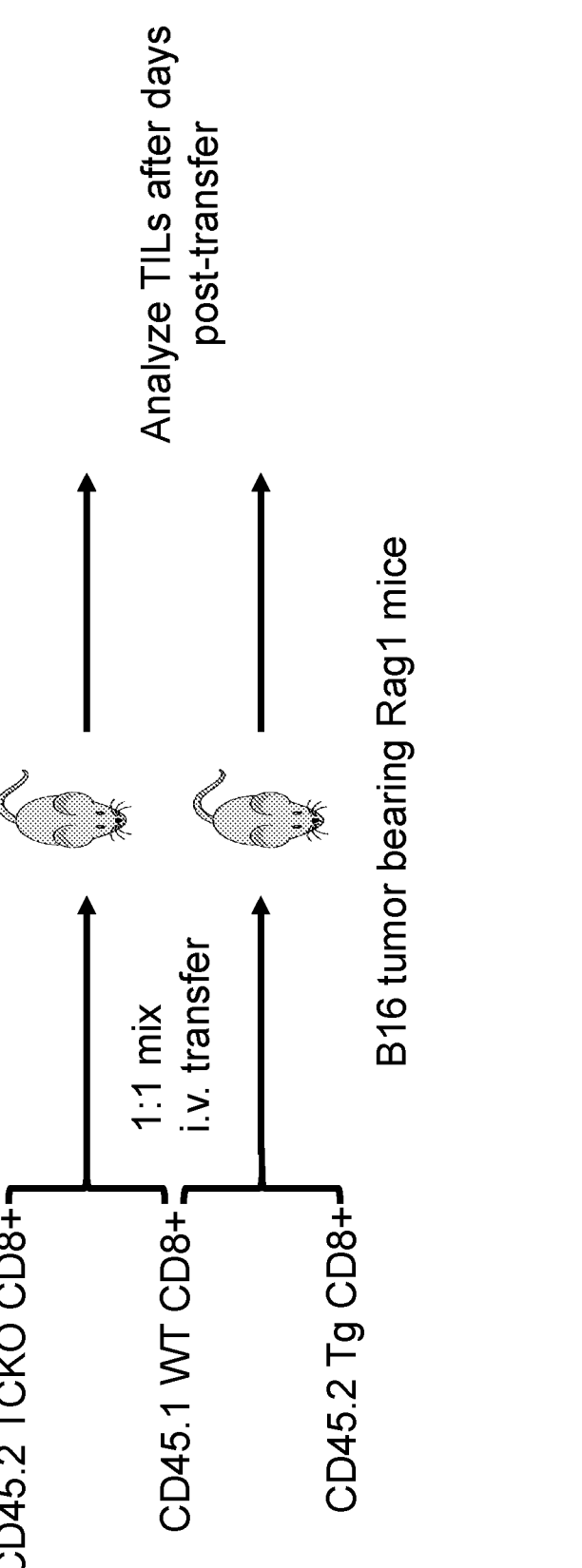
Figure 12C:
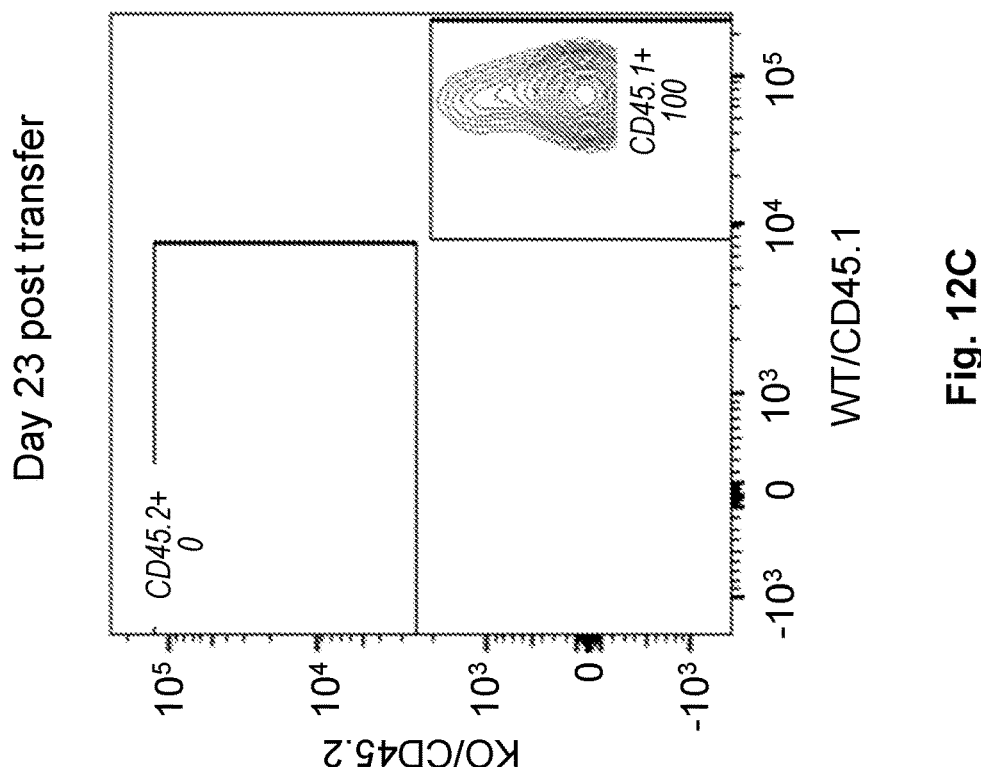
Figure 12B:
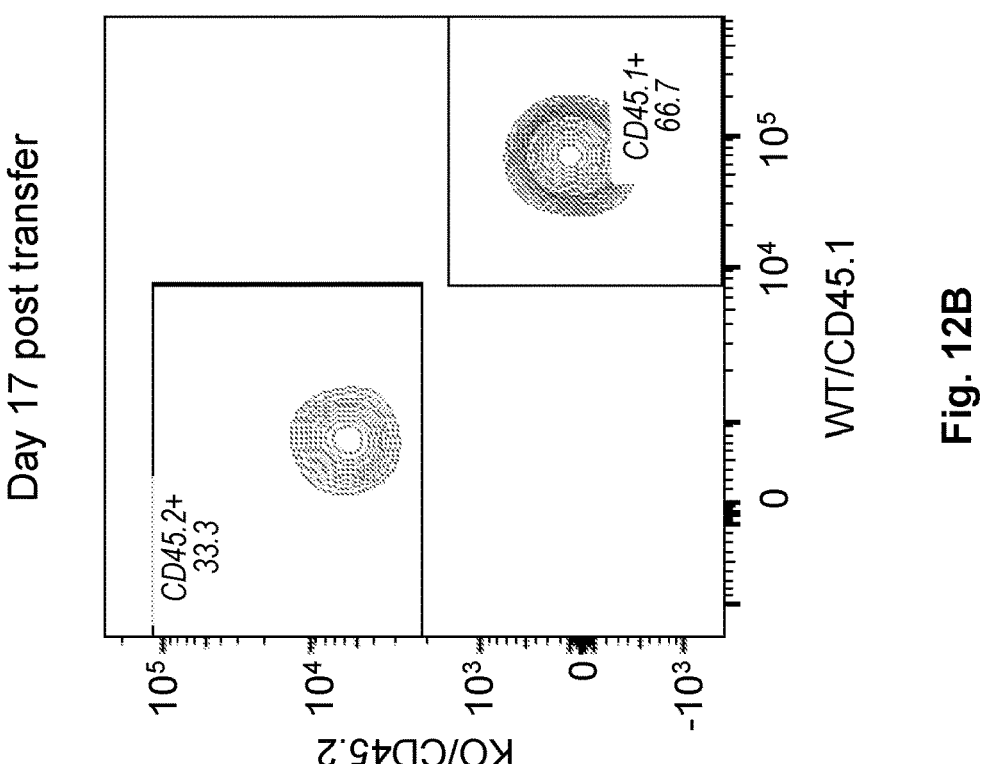
Figure 12D:
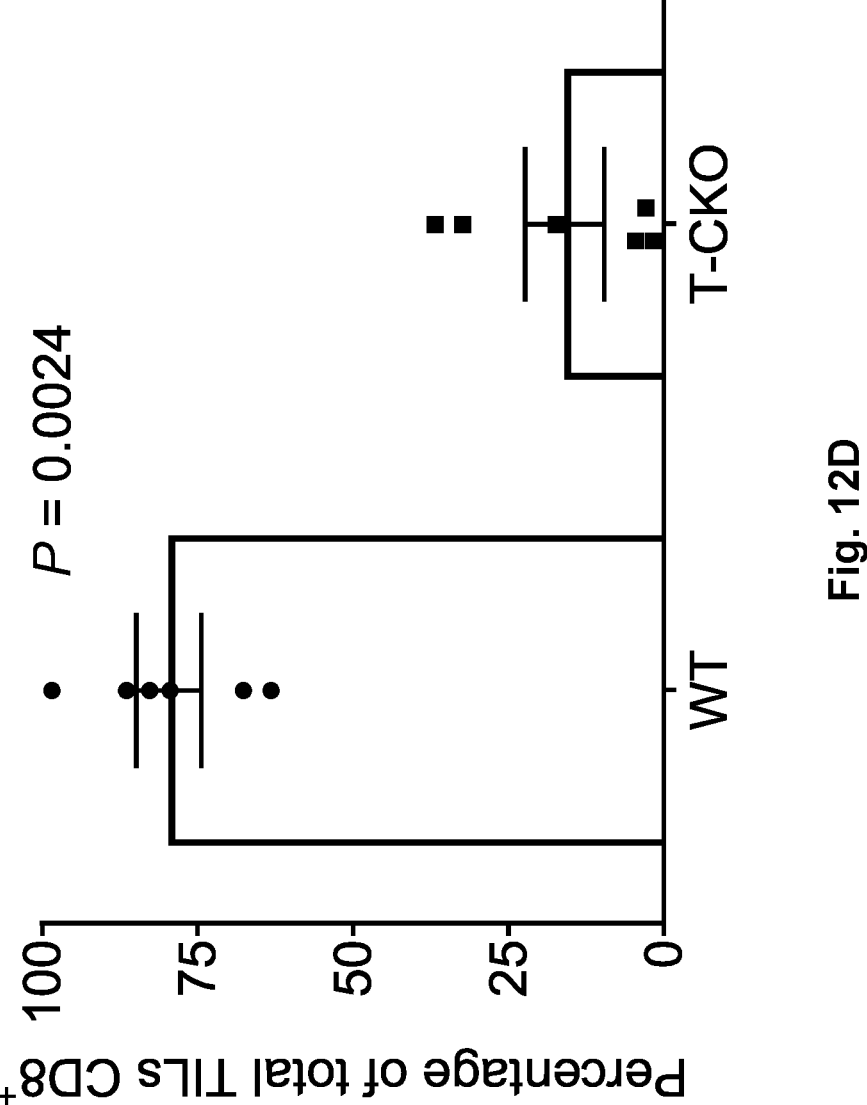
Figure 12F:
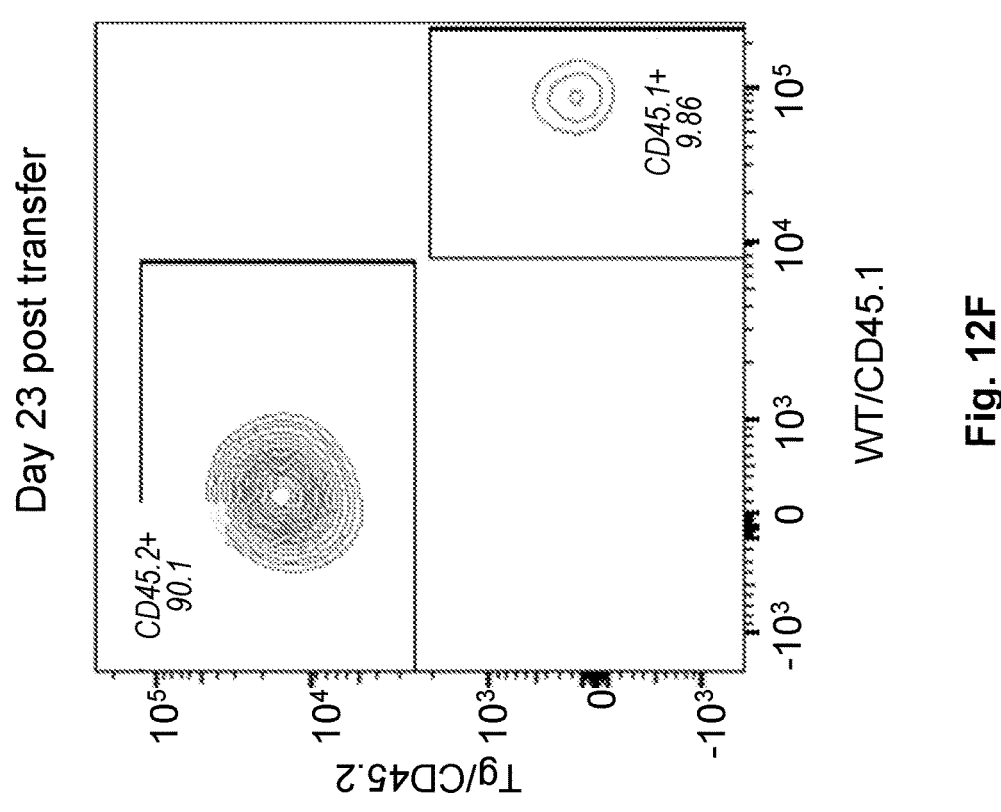
Figure 12E:
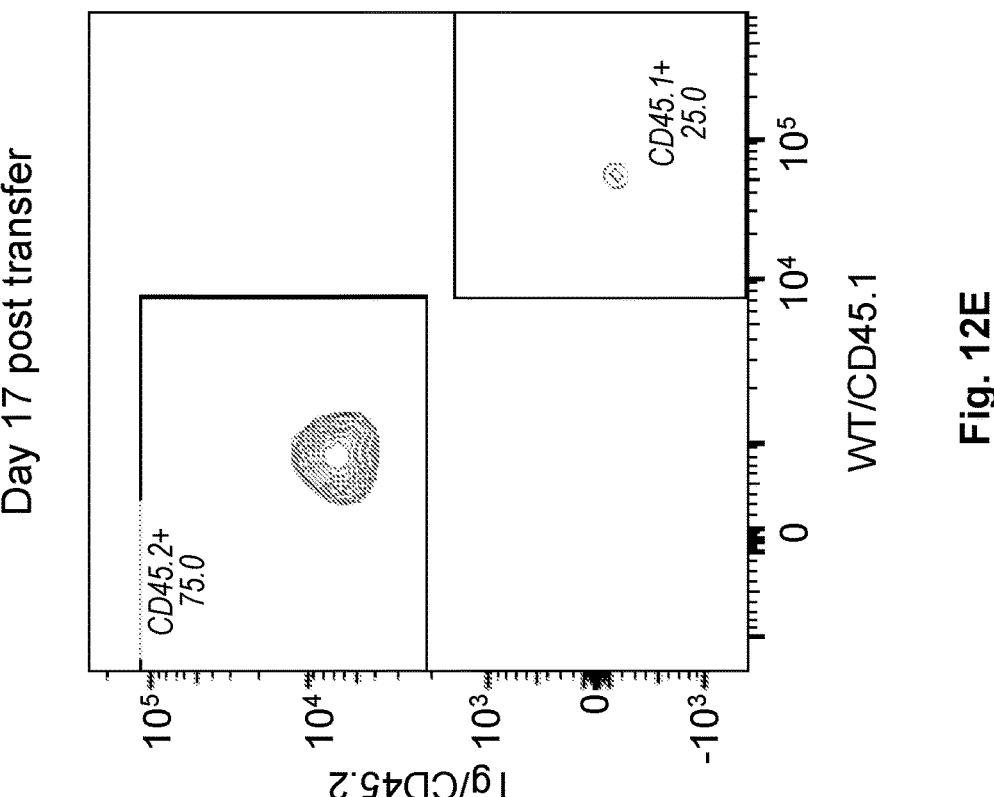
Figure 12G:
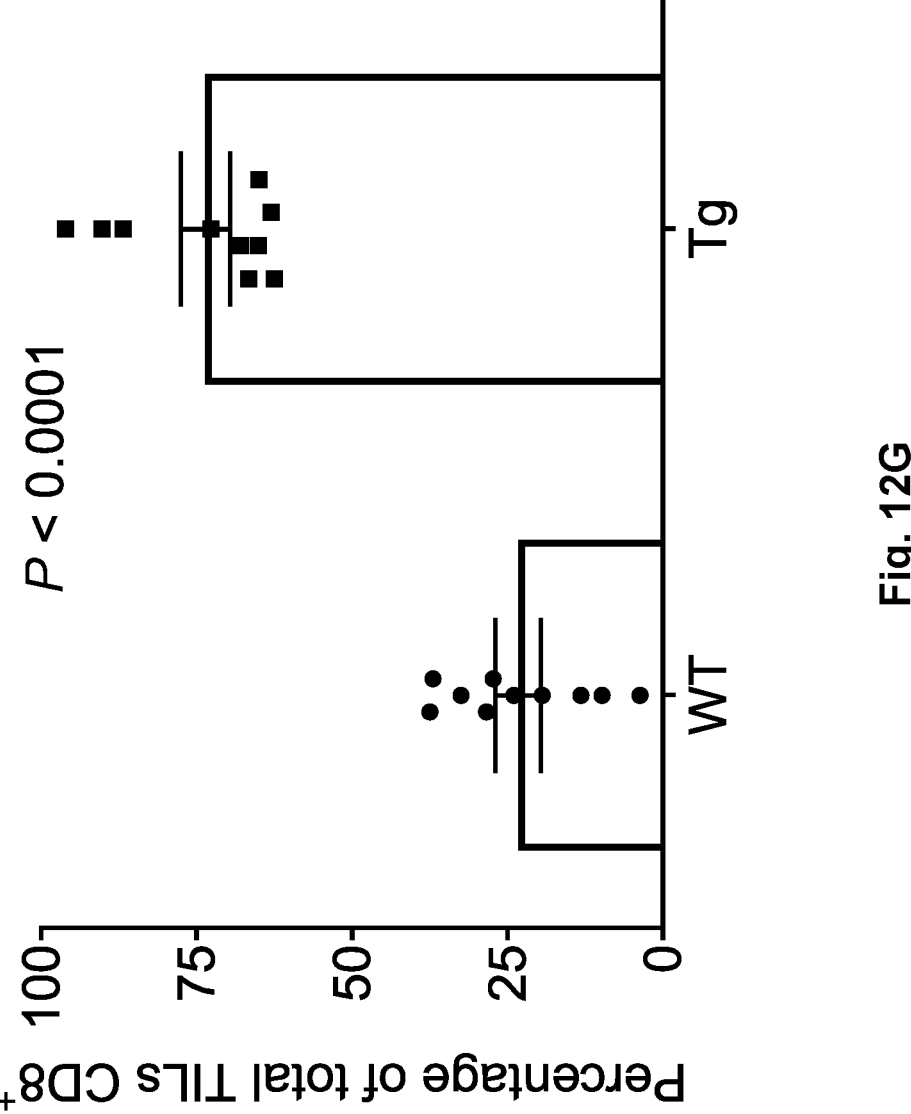

FIG. 12A is a diagram showing the experimental design. FIG. 12B is a scatterplot showing the percent of wildtype (CD45.1) and T-CKO (CD45.2) T cells in mice 17 days post transfer of wildtype and T-CKO T cells. FIG. 12C is a scatterplot showing the percent of wildtype (CD45.1) and T-CKO (CD45.2) T cells in mice 23 days post transfer of wildtype and T-CKO T cells. FIG. 12D is a graph showing the percent of total tumor infiltrating CD8+ T cells that are wildtype or T-CKO in mice that were administered a mixture of wildtype and T-CKO T cells. FIG. 12E is a scatterplot showing the percent of wildtype (CD45.1) and Tg (CD45.2) T cells in mice 17 days post transfer of wildtype and Tg T cells. FIG. 12F is a scatterplot showing the percent of wildtype (CD45.1) and Tg (CD45.2) T cells in mice 23 days post transfer of wildtype and Tg T cells. FIG. 12G is a graph showing the percent of total tumor infiltrating CD8+ T cells that are wildtype or Tg in mice that were administered a mixture of wildtype and Tg T cells.

Figure 13A:
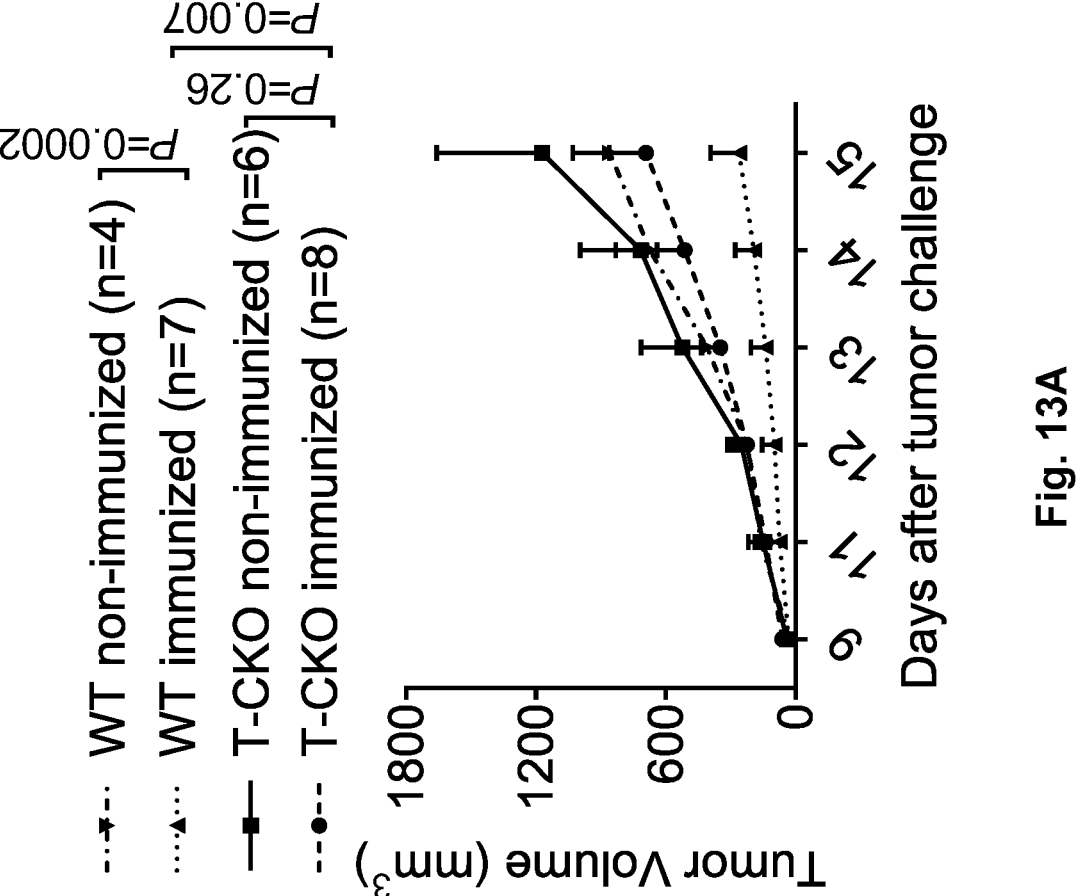
Figure 13C:
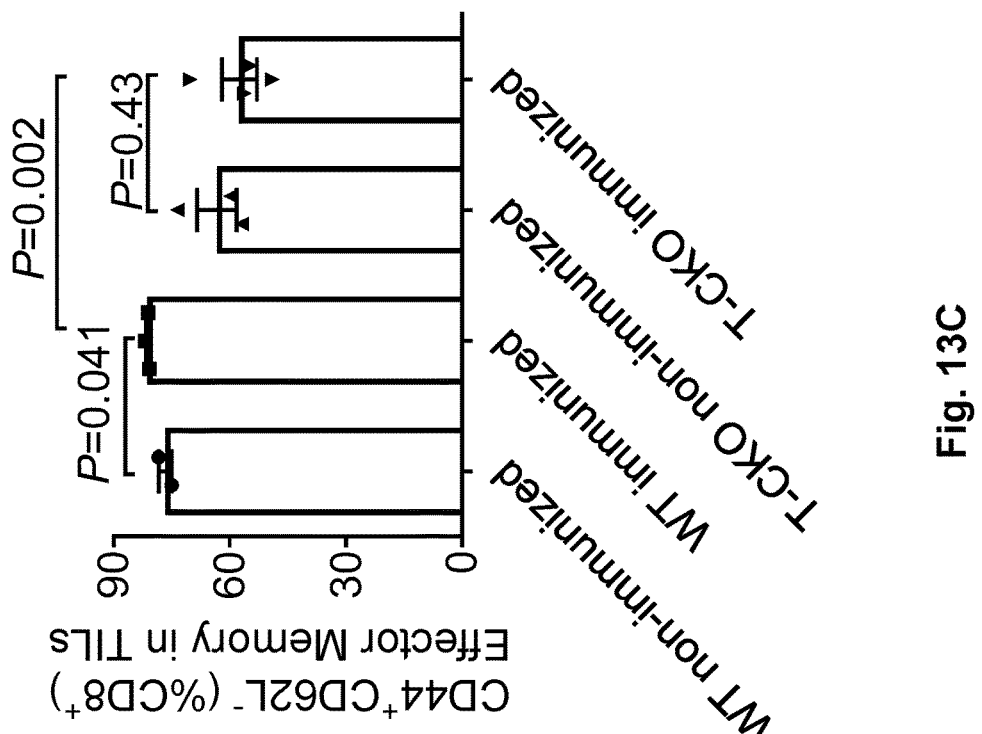
Figure 13B:
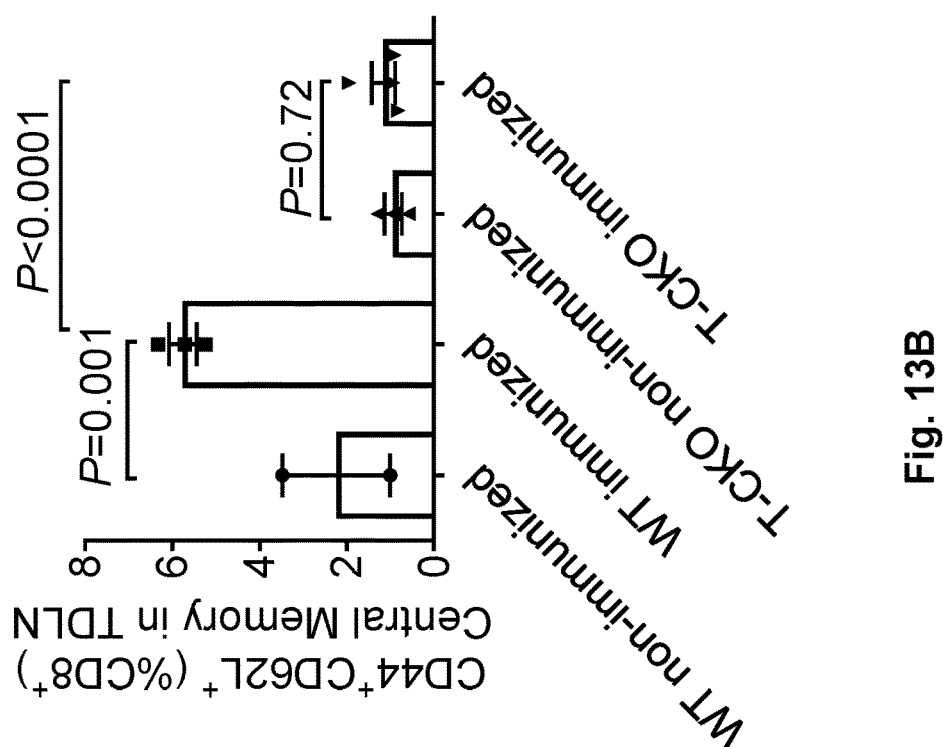

FIG. 13 shows tumor volume, percent of central memory T cells, and effector memory T cells in immunized and non-immunized wildtype and T-CKO (Cobra 1 knockout) mice. FIG. 13A is a graph showing tumor volume in immunized and non-immunized wildtype and T-CKO two weeks after injection with B16 tumor cells. FIG. 13B is a graph showing the percent of CD44+CD62L+CD8+ central memory T cells in tumor draining lymph nodes from immunized and non-immunized wildtype and T-CKO mice. FIG. 13C is a graph showing the percent of CD44+CD62L-CD8+ effector memory T cells in tumor infiltrating lymphocytes from immunized and non-immunized wildtype and T-CKO mice.

FIG. 14 shows the survival, percent of CD45+CD3+, and percent of CD8+ tumor infiltrating T cells in ovalbumin vaccinated and non-vaccinated wildtype and T-CKO (Cobra1 knockout) mice. FIG. 14A is a graph showing the percent survival of vaccinated and non-vaccinated wildtype and T-CKO mice after injection with E.G7-OVA lymphoma cells. FIG. 14B is a graph showing the percent of live CD45+CD3+ tumor infiltrating T cells in vaccinated and non-vaccinated wildtype and T-CKO mice after injection with E.G7-OVA lymphoma cells. FIG. 14C is a graph showing the percent survival of vaccinated and non-vaccinated wildtype and T-CKO mice after injection with B16-OVA melanoma cells. FIG. 14D is a graph showing the percent of live CD8+ tumor infiltrating T cells in vaccinated and non-vaccinated wildtype and T-CKO mice after injection with B16-OVA melanoma cells.

FIG. 15 shows the immunophenotype of tumor infiltrating cells isolated from Rag1−/− mice that were inoculated with E0071 tumor cells and reconstituted with wildtype or Tg (Cobra1 overexpression) T cells. FIGS. 15A-15H the percent of CD45+ (FIG. 15A), CD8+ (FIG. 15B), Ki67+ (FIG. 15C), IFNγ+ (FIG. 15D), CD44+CD62L− effector memory (FIG. 15E), exhausted PD-1+ TIM3+ LAG3+ (FIG. 15F), TNFα+ (FIG. 15G), and polyfunctional IFNγ+TNFα+(FIG. 15H) T cells.

DETAILED DESCRIPTION OF THE INVENTION

In one aspect, the present disclosure provides a T cell comprising a transgene integrated at a first site within the genome of the T cell, wherein the transgene encodes a polypeptide that is a subunit of a negative elongation factor (NELF) complex. In another aspect, the transgene encodes a COBRA1 polypeptide. In another aspect, the transgene encodes a polypeptide having at least about 95%, at least about 97%, at least about 98%, at least about 99%, at least about 99.5%, or 100% sequence identity to SEQ ID NO: 2.

In another aspect, the transgene encodes a NELFA polypeptide. In another aspect, the transgene encodes a NELFC polypeptide. In another aspect, the transgene encodes a NELFD polypeptide. In another aspect, the transgene encodes a NELFE polypeptide.

In another aspect, the transgene encodes a polypeptide having at least about 95%, at least about 97%, at least about 98%, at least about 99%, at least about 99.5%, or 100% sequence identity to SEQ ID NO: 4, the transgene encodes a polypeptide having at least about 95%, at least about 97%, at least about 98%, at least about 99%, at least about 99.5%, or 100% sequence identity to SEQ ID NO: 6, the transgene encodes a polypeptide having at least about 95%, at least about 97%, at least about 98%, at least about 99%, at least about 99.5%, or 100% sequence identity to SEQ ID NO: 8, and the transgene encodes a polypeptide having at least about 95%, at least about 97%, at least about 98%, at least about 99%, at least about 99.5%, or 100% sequence identity to SEQ ID NO: 10.

In another aspect, the transgene is under control of a promoter that increases expression of the polypeptide relative to the endogenous level of expression of said polypeptide. In another aspect, the increased expression is at least 1.5 times the endogenous level, at least 2 times the endogenous level, at least 3 times the endogenous level, at least 5 times the endogenous level, or at least 10 times the endogenous level of said polypeptide.

In another aspect, the T cell further comprises a recombinant nucleic acid sequence encoding a chimeric antigen receptor (CAR) integrated at a second site within the genome of the T cell. In another aspect, the T cell further comprises a recombinant nucleic acid sequence encoding a chimeric antigen receptor (CAR) integrated at the first site within the genome of the T cell. In another aspect, an isolated population of T cells comprises a plurality of the T cells. In another aspect, a pharmaceutical composition comprises a therapeutically effective amount of the population of T cells and a pharmaceutically acceptable carrier. In another aspect, a therapeutically effective amount of the T cell is administered to treat cancer in a subject in need thereof.

In another aspect, a vector comprises the transgene. In another aspect, the vector is a lentiviral vector. In another aspect, a T cell comprises the vector. In another aspect, the T cell is a T lymphocyte or a cytotoxic T lymphocyte.

In another aspect, the T cell or population of T cells comprises autologous cells. In another aspect, the T cell or population of T cells comprises allogeneic cells.

In one aspect, the present disclosure provides a method of treating a cancer in a subject in need thereof, comprising administering to the subject a therapeutically effective amount of a T cell or population of T cells, wherein the T cell or population of T cells comprise a transgene integrated at a first site within the genome of the T cell, wherein the transgene encodes a polypeptide that is a subunit of a NELF complex.

In another aspect, the subunit of the NELF complex is COBRA1. In another aspect, the transgene encodes a polypeptide having at least about 95%, at least about 97%, at least about 98%, at least about 99%, at least about 99.5%, or 100% sequence identity to SEQ ID NO: 2.

In another aspect, the method further comprises introducing a recombinant nucleic acid sequence encoding a CAR into the T cell or population of T cells.

In another aspect, the T cell or population of T cells comprises autologous cells. In another aspect, the T cell or population of T cells comprises allogeneic cells.

In another aspect, the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

In one aspect, the present disclosure provides a method of generating a T cell comprising: introducing into a T cell (i) a transgene, and (ii) a homologous recombination system suitable for targeted integration of the transgene at site within the genome of the cell, whereby the homologous recombination system integrates the transgene at said site within the genome of the cell, and wherein expression of the transgene is increased relative to the endogenous expression level, wherein the transgene encodes a polypeptide that is a subunit of a NELF complex.

In another aspect, the subunit of the NELF complex is COBRA1. In another aspect, the transgene encodes a polypeptide having at least about 95%, at least about 97%, at least about 98%, at least about 99%, at least about 99.5%, or 100% sequence identity to SEQ ID NO: 2.

In one aspect, the present disclosure provides a composition comprising a population of isolated T cells modified to overexpress one or more of a subunit of a NELF complex. In another aspect, the population of isolated T cells are further modified to express a recombinant receptor. In another aspect, the recombinant receptor is a T cell receptor (TCR). In another aspect, the recombinant receptor is a chimeric antigen receptor (CAR). In another aspect, the recombinant receptor is specific for a tumor antigen. In another aspect, the tumor antigen is selected from the group consisting of CD19, CD20, CD22, ROR1, GD2, EBV protein or antigen, folate receptor, Mesothelin, human carcinoembryonic antigen, CD33/IL3Ra, c-Met, PSMA, Glycolipid F77, EGFRvIII, NY-ESO-1, MAGE-A3, MART-1, GP1000 and p53.

In another aspect, the population of isolated T cells are native, naturally occurring T cells. In another aspect, the native, naturally occurring T cells are obtained from resected tumors. In another aspect, the native, naturally occurring T cells are obtained by leukapheresis of a blood sample. In another aspect, the T cells are expanded in vivo.

In another aspect, the population of isolated T cells are selected from the group consisting of CD3+ T cells, CD8+ T cells, CD4+ T cells, natural killer (NK) T cells, gamma delta T cells, a combination of CD4+ and CD8 T+ cells, memory T cells, cytokine-induced killer cells, and combinations thereof.

In one aspect, the present disclosure provides a method of enhancing a T cell immune response against cancer or infectious disease comprising overexpressing COBRA1 in the T cell.

Definitions

The term "Negative Elongation Factor Complex," "NELF complex," refers to a four subunit complex comprising the subunits NELF-A, NELF-B, NELF-E and either NELF-C or NELF-D.

The term "subunit of the NELF complex" as used herein, refers to any one or more of the following proteins: NELF-A, NELF-B (COBRA1), NELF-C, NELF-D, and NELF-E.

The term "COBRA1," "NELF-B," "negative elongation factor complex member B," or "cofactor of BRCA1" as used herein, includes any variants or isoforms of NELF-B that are naturally expressed by cells.

TABLE 1

| NELF Complex Subunit Nucleic Acids | | |
| --- | --- | --- |
| Subunit | SEQ ID NO | Sequence |
| NELF-A (Accession Number: NM_005663) | 3 | ATGGCGTCCATGCGGGAGAGCGACACGGGCCTGTGGCTGCACAACAA GCTGGGGGCCACGGACGAGCTGTGGGCGCCGCCCAGCATCGCGTCCC TGCTCACGGCCGCGGTCATCGACAACATCCGTCTCTGCTTCCATGGC CTCTCGTCGGCAGTGAAGCTCAAGTTGCTACTCGGGACGCTGCACCT CCCGCGCCGCACGGTGGACGAGATGAAGGGCGCCCTAATGGAGATCA TCCAGCTCGCCAGCCTCGACTCGGACCCCTGGGTGCTCATGGTCGCC GACATCTTGAAGTCCTTTCCGGACACAGGCTCGCTTAACCTGGAGCT GGAGGAGCAGAATCCCAACGTTCAGGATATTTTGGGAGAACTTAGAG AAAAGGTGGGTGAGTGTGAAGCGTCTGCCATGCTGCCACTGGAGTGC CAGTACTTGAACAAAAACGCCCTGACGACCCTCGCGGGACCCCTCAC TCCCCCGGTGAAGCATTTTCAGTTAAAGCGGAAACCCAAGAGCGCCA CGCTGCGGGCGGAGCTGCTGCAGAAGTCCACGGAGACCGCCCAGCAG TTGAAGCGGAGCGCCGGGGTGCCCTTCCACGCCAAGGGCCGGGGGCT GCTGCGGAAGATGGACACCACCACCCCACTCAAAGGCATCCCGAAGC AGGCGCCCTTCAGAAGCCCCACGGCGCCCAGCGTCTTCAGCCCCACA GGGAACCGGACCCCCATCCCGCCTTCCAGGACGCTGCTGCGGAAGGA ACGAGGTGTGAAGCTGCTGGACATCTCTGAGCTGGATATGGTTGGCG CTGGCCGAGAGGCGAAGCGGAGAAGGAAGACTCTCGATGCGGAGGTG GTGGAGAAGCCGGCCAAGGAGGAAACGGTGGTGGAGAACGCCACCCC GGACTACGCAGCCGGCCTGGTGTCCACGCAGAAACTTGGGTCCCTGA ACAATGAGCCTGCGCTGCCCTCCACGAGCTACCTTCCCTCCACGCCC AGCGTGGTTCCCGCCTCCTCCTACATCCCCAGCTCCGAGACGCCCCC AGCCCCATCTTCCCGGGAAGCCAGCCGCCCACCAGAGGAGCCCAGCG CCCCGAGCCCCACGTTGCCAGCGCAGTTCAAGCAGCGGGCGCCCATG TACAACAGCGGCCTGAGCCCTGCCACACCCACGCCTGCGGCGCCCAC CTCGCCTCTGACACCCACCACACCTCCGGCTGTCGCCCCTACCACTC AGACACCCCCGGTTGCCATGGTGGCCCCGCAGACCCAGGCCCCTGCT CAGCAGCAGCCTAAGAAGAACCTGTCCCTCACGAGAGAGCAGATGTT CGCTGCCCAGGAGATGTTCAAGACGGCCAACAAAGTCACGCGGCCCG AGAAGGCCCTCATCCTGGGCTTCATGGCCGGCTCCCGAGAGAACCCG TGCCAGGAGCAGGGGGACGTGATCCAGATCAAGCTGAGCGAGCACAC GGAGGACCTGCCCAAGGCGGACGGCCAGGGTAGCACAACCATGCTGG TGGACACAGTGTTTGAGATGAACTATGCCACGGGCCAGTGGACGCGC TTCAAGAAGTACAAGCCCATGACCAATGTGTCCTAG |
| NELF-B (Accession Number: NM_015456) | 1 | CTGGCCGAGCTGGAGGGCGCCGGGGAGCGGGGCTCGGGCGGTCCCCG AGGCCCGGCGGAGCGGGCTTCTGGGGTGTCTGCGGCGGCGCCGGGGG AACGGGCTGGGGATGGGGCGCCTAGCCGGGCGGTGGCCGGGGCCTCG GCCATGTTCGCGGGGCTGCAGGACCTGGGCGTGGCCAACGGCGAGGA CCTGAAGGAGACCCTGACCAACTGCACGGAGCCGCTCAAGGCCATCG AGCAGTTCCAGACAGAGAATGGTGTGCTGCTGCCATCTCTTCAGTCA GCCCTCCCCTTCTTGGACCTGCACGGGACGCCGCGGCTGGAGTTCCA CCAGTCGGTATTCGATGAGCTGCGGGACAAGCTGCTGGAGCGAGTGT CAGCCATCGCTTCGGAGGGGAAGGCTGAGGAAAGGTACAAGAAGCTG GAAGACCTTCTGGAGAAGAGCTTTTCTCTGGTGAAGATGCCGTCCCT GCAGCCCGTGGTGATGTGCGTCATGAAGCACCTGCCCAAGGTTCCGG AGAAAAAACTGAAGCTGGTTATGGCTGACAAGGAGCTGTATCGAGCC TGCGCCGTGGAGGTGAAGCGGCAGATCTGGCAAGACAACCAGGCCCT |

TABLE 1-continued

| | SEQ ID | |
|---|---|---|
| Subunit | NO | Sequence |
| | | CTTCGGGGACGAGGTTTCCCCACTCCTGAAGCAGTACATCCTGGAGA |
| | | AGGAGAGCGCTCTCTTCAGTACAGAGCTCTCTGTCCTGCACAACTTT |
| | | TTCAGTCCTTCCCCCAAGACCAGGCGCCAGGGCGAGGTGGTGCAGCG |
| | | GCTGACGCGGATGGTGGGGAAGAACGTGAAGCTGTACGACATGGTGC |
| | | TGCAGTTTCTGCGCACGCTCTTCCTGCGCACGCGGAATGTGCACTAC |
| | | TGCACGCTGCGGGCTGAGCTGCTCATGTCCCTGCACGACCTGGACGT |
| | | GGGTGAAATCTGCACCGTGGACCCGTGCCACAAGTTCACCTGGTGCC |
| | | TGGACGCCTGCATCCGAGAGCGGTTCGTGGACAGCAAGAGGGCGCGG |
| | | GAGCTGCAGGGGTTTCTCGATGGCGTCAAGAAGGGCCAGGAGCAGGT |
| | | GCTGGGGGACCTGTCCATGATCCTGTGTGACCCCTTCGCCATCAACA |
| | | CGCTGGCACTGAGCACAGTCAGGCACCTGCAGGAGCTGGTCGGCCAG |
| | | GAGACACTGCCCAGGGACAGCCCCGACCTCCTGCTGCTGCTCCGGCT |
| | | GCTGGCGCTGGGCCAGGGAGCCTGGGACATGATCGACAGCCAGGTCT |
| | | TCAAGGAGCCCAAGATGGAGGTAGAGCTCATCACCAGGTTCCTCCCG |
| | | ATGCTCATGTCCTTCCTGGTGGATGACTACACTTTCAATGTGGATCA |
| | | GAAACTTCCGGCTGAGGAGAAAGCCCCAGTCTCATATCCAAACACAC |
| | | TTCCCGAAAGCTTCACTAAGTTTCTGCAGGAGCAGCGCATGGCCTGC |
| | | GAGGTGGGGCTGTACTACGTCCTGCACATCACCAAGCAGAGGAACAA |
| | | GAACGCGCTCCTCCGCCTGCTGCCCGGGCTGGTGGAGACCTTTGGCG |
| | | ACTTGGCCTTTGGCGACATCTTCCTCCACCTGCTCACGGGCAACCTT |
| | | GCGCTGCTGGCCGACGAATTTGCCCTTGAGGACTTCTGCAGCAGCCT |
| | | CTTCGATGGCTTCTTCCTCACCGCCTCTCCAAGGAAGGAGAACGTGC |
| | | ACCGGCACGCGCTGCGGCTCCTCATTCACCTGCACCCCAGGGTGGCC |
| | | CCGTCTAAGCTGGAGGCGTTGCAGAAGGCCCTGGAGCCTACAGGCCA |
| | | GAGCGGAGAGGCAGTGAAGGAGCTTTACTCCCAGCTCGGCGAGAAGC |
| | | TGGAACAGCTGGATCACCGGAAGCCCAGCCCGGCACAGGCTGCGGAG |
| | | ACGCCGGCCCTGGAGCTGCCCCTCCCCAGCGTGCCCGCCCCTGCCCC |
| | | GCTCTGA |
| NELF-C (Accession Number: NM_198976) | 5 | ATGGCGGGGGCCGTGCCGGGCGCCATCATGGACGAGGACTACTACGG |
| | | GAGCGCGGCCGAGTGGGGCGACGAGGCTGACGGCGGCCAGCAGGAGG |
| | | ATGATTCTGGAGAAGGAGAGGATGATGATGCGGAGGTTCAGCAAGAATGC |
| | | CTGCATAAATTTTCCACCCGGGATTATATCATGGAACCCTCCATCTT |
| | | CAACACTCTGAAGAGGTATTTTCAGGCAGGAGGGTCTCCAGAGAATG |
| | | TTATCCAGCTCTTATCTGAAAACTACACCGCTGTGGCCCAGACTGTG |
| | | AACCTGCTGGCCGAGTGGCTCATTCAGACAGGTGTTGAGCCAGTGCA |
| | | GGTTCAGGAAACTGTGGAAAATCACTTGAAGAGTTTGCTGATCAAAC |
| | | ATTTTGACCCCCGCAAAGCAGATTCTATTTTTACTGAAGAAGGAGAG |
| | | ACCCCAGCGTGGCTGGAACAGATGATTGCACATACCACGTGGCGGGA |
| | | CCTTTTTTATAAACTGGCTGAAGCCCATCCAGACTGTTTGATGCTGA |
| | | ACTTCACCGTTAAGCTTATTTCTGACGCAGGGTACCAGGGGGAGATC |
| | | ACCAGTGTGTCCACAGCATGCCAGCAGCTAGAAGTGTTCTCGAGAGT |
| | | GCTCCGGACCTCTCTAGCTACAATTTTAGATGGAGGAGAAGAAACC |
| | | TTGAAAAAAATCTCCCTGAGTTTGCCAAGATGGTGTGCCACGGGGAG |
| | | CACACGTACCTGTTTGCCCAGGCCATGATGTCCGTGCTGGCCCAGGA |
| | | GGAGCAGGGGGGCTCCGCTGTGCGCAGGATCGCCCAGGAAGTGCAGC |
| | | GCTTTGCCCAGGAGAAAGGTCATGACGCCAGTCAGATCACACTAGCC |
| | | TTGGGCACAGCTGCCTCCTACCCCAGGGCCTGCCAGGCTCTCGGGGC |
| | | CATGCTGTCCAAAGGAGCCCTGAACCCTGCTGACATCACCGTCCTGT |
| | | TCAAGATGTTCACAAGCATGGACCCTCCTCCGGTTGAACTTATCCGC |
| | | GTTCCAGCCTTCCTGGACCTGTTCATGCAGTCACTCTTTAAACCAGG |
| | | GGCTCGGATCAACCAGGACCACAAGCACAAATACATCCACATCTTGG |
| | | CGTACGCAGCAAGCGTGGTTGAGACCTGGAAGAAGAACAAGCGAGTG |
| | | AGCATCAATAAAGATGAGCTGAAGTCAACGTCAAAAGCTGTCGAAAC |
| | | CGTTCACAATTTGTGTTGCAACGAGAACAAAGGGGCCTCTGAACTAG |
| | | TGGCAGAATTGAGCACACTTTATCAGTGTATTAGGTTTCCAGTGGTA |
| | | GCAATGGGTGTGCTGAAGTGGGTGGATTGGACTGTATCAGAACCAAG |
| | | GTACTTTCAGCTGCAGACTGACCATACCCCTGTCCACCTGGCGTTGC |
| | | TGGATGAGATCAGCACCTGCCACCAGCTCCTGCACCCCCAGGTCCTG |
| | | CAGCTGCTTGTTAAGCTTTTTGAGACTGAGCACTCCCAGCTGGACGT |
| | | GATGGAGCAGCTTGAGTTGAAGAAGACACTGCTGGACAGGATGGTTC |
| | | ACCTGCTGAGTCGAGGTTATGTACTTCCTGTTGTCAGTTACATCCGA |
| | | AAGTGTCTGGAGAAGCTGGACACTGACATTTCACTCATTCGCTATTT |
| | | TGTCACTGAGGTGCTGGACGTCATTGCTCCTCCTTATACCTCTGACT |
| | | TCGTGCAACTTTTCCTCCCCATCCTGGAGAATGACAGCATCGCAGGT |
| | | ACCATCAAAACGGAAGGCGAGCATGACCCTGTGACGGAGTTTATAGC |
| | | TCACTGCAAATCTAACTTCATCATGGTGAACTAA |
| NELF-D (Accession Number: NM_198976) | 7 | ATGGACGAGGACTACTACGGGAGCGCGGCCGAGTGGGGCGACGAGGC |
| | | TGACGGCGGCCAGCAGGAGGATGATTCTGGAGAAGGAGAGGATGATG |
| | | CGGAGGTTCAGCAAGAATGCCTGCATAAATTTTCCACCCGGGATTAT |
| | | ATCATGGAACCCTCCATCTTCAACACTCTGAAGAGGTATTTTCAGGC |
| | | AGGAGGGTCTCCAGAGAATGTTATCCAGCTCTTATCTGAAAACTACA |
| | | CCGCTGTGGCCCAGACTGTGAACCTGCTGGCCGAGTGGCTCATTCAG |

TABLE 1-continued

| | | NELF Complex Subunit Nucleic Acids |
|---|---|---|
| Subunit | SEQ ID NO | Sequence |
| | | ACAGGTGTTGAGCCAGTGCAGGTTCAGGAAACTGTGGAAAATCACTT |
| | | GAAGAGTTTGCTGATCAAACATTTTGACCCCCGCAAAGCAGATTCTA |
| | | TTTTTACTGAAGAAGGAGAGACCCCAGCGTGGCTGGAACAGATGATT |
| | | GCACATACCACGTGGCGGGACCTTTTTTATAAACTGGCTGAAGCCCA |
| | | TCCAGACTGTTTGATGCTGAACTTCACCGTTAAGCTTATTTCTGACG |
| | | CAGGGTACCAGGGGGAGATCACCAGTGTGTCCACAGCATGCCAGCAG |
| | | CTAGAAGTGTTCTCGAGAGTGCTCCGGACCTCTCTAGCTACAATTTT |
| | | AGATGGAGGAGAAGAAACCTTGAAAAAAATCTCCCTGAGTTTGCCA |
| | | AGATGGTGTGCCACGGGGAGCACACGTACCTGTTTGCCCAGGCCATG |
| | | ATGTCCGTGCTGGCCCAGGAGGAGCAGGGGGGCTCCGCTGTGCGCAG |
| | | GATCGCCCAGGAAGTGCAGCGCTTTGCCCAGGAGAAAGGTCATGACG |
| | | CCAGTCAGATACACACTAGCCTTGGGCACAGCTGCCTCCTACCCCAGG |
| | | GCCTGCCAGGCTCTCGGGGCCATGCTGTCCAAAGGAGCCCTGAACCC |
| | | TGCTGACATCACCGTCCTGTTCAAGATGTTCACAAGCATGGACCCTC |
| | | CTCCGGTTGAACTTATCCGCGTTCCAGCCTTCCTGGACCTGTTCATG |
| | | CAGTCACTCTTTAAACCAGGGGCTCGGATCAACCAGGACCACAAGCA |
| | | CAAATACATCCACATCTTGGCGTACGCAGCAAGCGTGGTTGAGACCT |
| | | GGAAGAAGAACAAGCGAGTGAGCATCAATAAAGATGAGCTGAAGTCA |
| | | ACGTCAAAAGCTGTCGAAACCGTTCACAATTTGTGTTGCAACGAGAA |
| | | CAAAGGGGCCTCTGAACTAGTGGCAGAATTGAGCACACTTTATCAGT |
| | | GTATTAGGTTTCCAGTGGTAGCAATGGGTGTGCTGAAGTGGGTGGAT |
| | | TGGACTGTATCAGAACCAAGGTACTTTCAGCTGCAGACTGACCATAC |
| | | CCCTGTCCACCTGGCGTTGCTGGATGAGATCAGCACCTGCCACCAGC |
| | | TCCTGCACCCCCAGGTCCTGCAGCTGCTTGTTAAGCTTTTTGAGACT |
| | | GAGCACTCCCAGCTGGACGTGATGGAGCAGCTTGAGTTGAAGAAGAC |
| | | ACTGCTGGACAGGATGGTTCACCTGCTGAGTCGAGGTTATGTACTTC |
| | | CTGTTGTCAGTTACATCCGAAAGTGTCTGGAGAAGCTGGACACTGAC |
| | | ATTTCACTCATTCGCTATTTTGTCACTGAGGTGCTGGACGTCATTGC |
| | | TCCTCCTTATACCTCTGACTTCGTGCAACTTTTCCTCCCCATCCTGG |
| | | AGAATGACAGCATCGCAGGTACCATCAAAACGGAAGGCGAGCATGAC |
| | | CCTGTGACGGAGTTTATAGCTCACTGCAAATCTAACTTCATCATGGT |
| | | GAACTAA |
| NELF-E (Accession Number: NM_002904) | 9 | ATGTTGGTGATACCCCCCGGACTGAGCGAGGAAGAGGAGGCTCTGCA |
| | | GAAGAAATTCAACAAGCTCAAGAAAAAGAAAAAGGCATTGCTGGCTC |
| | | TGAAGAAGCAAAGTAGCAGCAGCACAACCAGCCAAGGTGGTGTCAAA |
| | | CGCTCACTATCAGAGCAGCCTGTCATGGACACAGCCACAGCAACAGA |
| | | GCAGGCAAAGCAGCTGGTGAAGTCAGGAGCCATCAGTGCCATCAAGG |
| | | CTGAGACCAAGAACTCAGGCTTCAAGCGTTCTCGAACCCTTGAGGGG |
| | | AAGTTAAAGGACCCCGAGAAGGGACCAGTCCCCACTTTCCAGCCGTT |
| | | CCAGAGGAGCATATCTGCTGATGATGACCTGCAAGAGTCATCCAGAC |
| | | GTCCCCAGAGGAAATCTCTGTATGAGAGCTTTGTGTCTTCTAGTGAT |
| | | CGACTTCGAGAACTAGGACCAGATGGAGAAGAGGCAGAGGGCCCAGG |
| | | GGCTGGTGATGGTCCCCCTCGAAGCTTTGACTGGGGCTATGAAGAAC |
| | | GCAGTGGTGCCCACTCCTCAGCCTCCCCTCCCCGAAGCCGCAGCCGG |
| | | GACCGCAGCCATGAGAGGAACCGGGACAGAGACCGAGATCGGGAGCG |
| | | GGATCGAGACCGGGATCGAGACAGAGACAGAGAGCGGGACAGGGATC |
| | | GGGATCGGGATCGAGATCGAGACCGGGAACGGGACAGGGATCGGGAG |
| | | CGGGATCGAGACCGAGACCGAGAGGGTCCTTTCCGCAGGTCGGATTC |
| | | ATTCCCTGAACGGCGAGCCCCTAGGAAAGGGAATACTCTCTATGTAT |
| | | ATGGAGAAGACATGACACCCACCCTTCTCCGTGGGGCCTTCTCTCCT |
| | | TTTGGAAACATCATTGACCTCTCCATGGACCCACCCAGAAACTGTGC |
| | | CTTCGTCACCTATGAAAAGATGGAGTCAGCAGATCAGGCCGTTGCTG |
| | | AGCTCAACGGGACCCAGGTGGAGTCTGTACAGCTCAAAGTCAACATA |
| | | GCCCGAAAACAGCCCATGCTGGATGCCGCTACTGGCAAGTCTGTCTG |
| | | GGGCTCCCTCGCTGTCCAGAACAGCCCTAAGGGTTGCCACCGGGACA |
| | | AGAGGACCCAGATTGTCTACAGTGATGACGTCTACAAGGAAAACCTT |
| | | GTGGATGGCTTCTAG |

TABLE 2

| | | NELF Complex Subunit Polypeptides |
|---|---|---|
| Subunit | SEQ ID NO | Sequence |
| NELF-A (Accession Number: NP_005654) | 4 | MASMRESDTGLWLHNKLGATDELWAPPSIASLLTAAVIDNIRLCFHGLSSA VKLKLLLGTLHLPRRTVDEMKGALMEIIQLASLDSDPWVLMVADILKSFPD TGSLNLELEEQNPNVQDILGELREKVGECEASAMLPLECQYLNKNALTTLA GPLTPPVKHFQLKRKPKSATLRAELLQKSTETAQQLKRSAGVPFHAKGRGL |

TABLE 2-continued

NELF Complex Subunit Polypeptides

| Subunit | SEQ ID NO | Sequence |
|---|---|---|
| | | LRKMDTTTPLKGIPKQAPFRSPTAPSVFSPTGNRTPIPPSRTLLRKERGVK LLDISELDMVGAGREAKRRRKTLDAEVVEKPAKEETVVENATPDYAAGLVS TQKLGSLNNEPALPSTSYLPSTPSVVPASSYIPSSETPPAPSSREASRPPE EPSAPSPTLPAQFKQRAPMYNSGLSPATPTPAAPTSPLTPTTPPAVAPTTQ TPPVAMVAPQTQAPAQQQPKKNLSLTREQMFAAQEMFKTANKVTRPEKALI LGFMAGSRENPCQEQGDVIQIKLSEHTEDLPKADGQGSTTMLVDTVFEMNY ATGQWTRFKKYKPMTNVS |
| NELF-B (Accession Number: NP_056271) | 2 | MAELEGAGERGSGGPRGPAERASGVSAAAPGERAGDGAPSRAVAGASAMFA GLQDLGVANGEDLKETLTNCTEPLKAIEQFQTENGVLLPSLQSALPFLDLH GTPRLEFHQSVFDELRDKLLERVSAIASEGKAEERYKKLEDLLEKSFSLVK MPSLQPVVMCVMKHLPKVPEKKLKLVMADKELYRACAVEVKRQIWQDNQAL FGDEVSPLLKQYILEKESALFSTELSVLHNFFSPSPKTRRQGEVVQRLTRM VGKNVKLYDMVLQFLRTLFLRTRNVHYCTLRAELLMSLHDLDVGEICTVDP CHKFTWCLDACIRERFVDSKRARELQGFLDGVKKGQEQVLGDLSMILCDPF AINTLALSTVRHLQELVGQETLPRDSPDLLLLLRLLALGQGAWDMIDSQVF KEPKMEVELITRFLPMLMSFLVDDYTFNVDQKLPAEEKAPVSYPNTLPESF TKFLQEQRMACEVGLYYVLHITKQRNKNALLRLLPGLVETFGDLAFGDIFL HLLTGNLALLADEFALEDFCSSLFDGFFLTASPRKENVHRHALRLLIHLHP RVAPSKLEALQKALEPTGQSGEAVKELYSQLGEKLEQLDHRKPSPAQAAET PALELPLPSVPAPAPL |
| NELF-C (Accession Number: Q8IXH7-1) | 6 | MAGAVPGAIMDEDYYGSAAEWGDEADGGQQEDDSGEGEDDAEVQQECLHKF STRDYIMEPSIFNTLKRYFQAGGSPENVIQLLSENYTAVAQTVNLLAEWLI QTGVEPVQVQETVENHLKSLLIKHFDPRKADSIFTEEGETPAWLEQMIAHT TWRDLFYKLAEAHPDCLMLNFTVKLISDAGYQGEITSVSTACQQLEVFSRV LRTSLATILDGGEENLEKNLPEFAKMVCHGEHTYLFAQAMMSVLAQEEQGG SAVRRIAQEVQRFAQEKGHDASQITLALGTAASYPRACQALGAMLSKGALN PADITVLFKMFTSMDPPPVELIRVPAFLDLFMQSLFKPGARINQDHKHKYI HILAYAASVVETWKKNKRVSINKDELKSTSKAVETVHNLCCNENKGASELV AELSTLYQCIRFPVVAMGVLKWVDWTVSEPRYFQLQTDHTPVHLALLDEIS TCHQLLHPQVLQLLVKLFETEHSQLDVMEQLELKKTLLDRMVHLLSRGYVL PVVSYIRKCLEKLDTDISLIRYFVTEVLDVIAPPYTSDFVQLFLPILENDS IAGTIKTEGEHDPVTEFIAHCKSNFIMVN |
| NELF-D (Accession Number: Q8IXH7-4) | 8 | MDEDYYGSAAEWGDEADGGQQEDDSGEGEDDAEVQQECLHKFSTRDYIMEP SIFNTLKRYFQAGGSPENVIQLLSENYTAVAQTVNLLAEWLIQTGVEPVQV QETVENHLKSLLIKHFDPRKADSIFTEEGETPAWLEQMIAHTTWRDLFYKL AEAHPDCLMLNFTVKLISDAGYQGEITSVSTACQQLEVFSRVLRTSLATIL DGGEENLEKNLPEFAKMVCHGEHTYLFAQAMMSVLAQEEQGGSAVRRIAQE VQRFAQEKGHDASQITLALGTAASYPRACQALGAMLSKGALNPADITVLFK MFTSMDPPPVELIRVPAFLDLFMQSLFKPGARINQDHKHKYIHILAYAASV VETWKKNKRVSINKDELKSTSKAVETVHNLCCNENKGASELVAELSTLYQC IRFPVVAMGVLKWVDWTVSEPRYFQLQTDHTPVHLALLDEISTCHQLLHPQ VLQLLVKLFETEHSQLDVMEQLELKKTLLDRMVHLLSRGYVLPVVSYIRKC LEKLDTDISLIRYFVTEVLDVIAPPYTSDFVQLFLPILENDSIAGTIKTEG EHDPVTEFIAHCKSNFIMVN |
| NELF-E (Accession Number: NP_002895) | 10 | MLVIPPGLSEEEEALQKKFNKLKKKKKALLALKKQSSSSTTSQGGVKRSLS EQPVMDTATATEQAKQLVKSGAISAIKAETKNSGFKRSRTLEGKLKDPEKG PVPTFQPFQRSISADDDLQESSRRPQRKSLYESFVSSSDRLRELGPDGEEA EGPGAGDGPPRSFDWGYEERSGAHSSASPPRSRSRDRSHERNRDRDRDRER DRDRDRDRDRERDRDRDRDRDRERDRDRERDRDRDREGPFRRSDSFPER RAPRKGNTLYVYGEDMTPTLLRGAFSPFGNIIDLSMDPPRNCAFVTYEKME SADQAVAELNGTQVESVQLKVNIARKQPMLDAATGKSVWGSLAVQNSPKGC HRDKRTQIVYSDDVYKENLVDGF |

EXAMPLES

Example 1

Generation of a T Cell Specific Cobra1 Knockout Mouse

A T cell specific Cobra1 knockout mouse was generated using a Cre/lox system. To confirm Cobra1 knockout, splenocytes were harvested from WT and T cell-specific Cobra1 knockout (T-CKO) mice and CD8+ T cells were isolated using a negative selection protocol. Genomic DNA PCR shows abundant Cobra1 minus allele in purified CD8+ cells, indicating that Cobra1 genomic sequence was successfully cleaved in CD8+ cells (FIG. 1). The same "minus" band was relatively weak in total splenocytes and non CD8+ T cells, demonstrating cell type specificity of the Cre action.

Next, expression level of Cobra1 and the other NELF complex subunits was examined. Splenocytes were harvested from WT and T cell-specific Cobra1 knockout (T-CKO) mice and CD8+ T cells were isolated using a negative selection protocol. Results show that Cobra1 and the other NELF subunits, the stability of which is known to be inter-dependent, were significantly reduced in T-CKO CD8+ cells (FIG. 2A). The quantification of individual protein abundance is shown in FIGS. 2B-2E. NELFB (Cobra1) had ~5.16 fold lower expression in T-CKO CD8+ T cells compared to WT CD8+ T cells (FIG. 2C).

Example 2

Anti-Tumor Immunity in Cobra1 T-Cell Specific Knockout Mice

Next, the effect of Cobra1 T-cell specific knockout on the growth of tumors was examined. 0.5 million mouse mammary tumor cells (E0771) were orthotopically inoculated into the mammary fat pad of WT and T-CKO mice. Tumor volume was monitored by digital caliper and calculated as 0.5×width×length. Tumors weights were measured upon harvest. T-CKO mice had significantly greater tumor volume and weight compared to WT mice (FIGS. 3A-3B). FIG. 3C shows an image of the tumor upon harvest.

Tumor immunophenotyping shows that there were fewer tumor-infiltrating CD8+ T cells in T-CKO compared to WT mice. Within the CD8+ T cell population, there were fewer effector memory T cells as defined by the established markers CD44+CD62L− (FIGS. 4A-4B). Additionally, CD8+ T cells from tumors in T-CKO hosts had a lower level of expression of Ki67 (proliferative marker) and GzmB (cytotoxic marker) compared to CD8+ T cells from tumors in WT hosts, suggesting weakened memory T cell function in Cobra1-deleted mice (FIGS. 4C-4D).

To further examine the effect of Cobra1 T-cell specific knockout on the growth of tumors, mice were inoculated with 0.5 million cells of mouse B16 melanoma cell line were into the back flank of WT and T-CKO mice. 0.2 million cells of mouse mammary tumor cell line AT-3 were inoculated into the mammary fat pad of WT and T-CKO mice. T-CKO mice had significantly greater tumor volume and weight compared to WT mice (FIGS. 5A-5B). Taken together, our results show that antitumor immunity is defective in T-CKO mice versus WT mice for multiple syngeneic tumor models (melanoma B16 and two different mammary tumor models AT-3 and E0771).

Example 3

Anti-Tumor Immunity After Adoptive Transfer of Cobra1 Knockout T Cells 3 million CD8+ cells purified from WT or T-CKO mice splenocytes were intravenously transferred into Rag1−/− immunodeficient mice. E0771 tumor cells were then inoculated into the Rag1−/− mice reconstituted with either WT or T-CKO CD8+ T cells. Results show that, in contrast to adoptively transferred WT CD8+ T cells that effectively killed tumor cells, CD8+ cells isolated from T-CKO mice lost the tumor-killing effects (FIGS. 6A-6B).

Despite the same number of WT and T-CKO CD8+ T cells transferred in the adoptive transfer experiment, analysis of tumor infiltrating lymphocytes (TILs) shows that T-CKO CD8+ cells are less abundant compared to WT CD8+ cells (FIG. 7A). Further phenotyping analysis reveals that T-CKO CD8+ cells express less of the effector memory T cell marker (CD44+CD62L−), and more of the naïve T cell marker (CD44-CD62L+), consistent with the notion that antitumor immunity is significantly attenuated in Cobra1 KO T cells (FIGS. 7B-7C).

The adoptive transfer experiment was repeated using the melanoma B16 tumor model. Like the results from the E0771 model, T-CKO CD8+ cells had defective tumor killing effects compared to WT CD8+ cells (FIG. 8).

Example 4

Anti-Tumor Immunity in Cobra1 T Cell Specific Transgenic Mice

To further examine the role of T cell specific expression in tumor growth, T cell specific Cobra1 transgenic mice were generated. Overexpression of Cobra1 (NELFB) was confirmed by Western blotting (FIG. 9A). 0.5 million CD8+ cells were isolated from parental WT and Tg mice and then intravenously transferred into Rag1−/− immunodeficient mice. E0771 tumor cells were then orthotopically inoculated into the mammary fat pad of Rag1−/− mice reconstituted with parental WT or Tg CD8+ T cells. Tumor images and weights were recorded upon harvest. Results show that Tg CD8+ had stronger antitumor killing effects compared to WT CD8+. (FIGS. 9B-9D). Immunophenotyping analysis shows that Tg had more CD8+ cells in the spleen (FIG. 9E) and tumor-infiltrating lymphocytes (FIG. 9F) as compared to the parental WT group.

CD8+ adoptive transfer experiments were repeated using B16 melanoma cells in both male and female T cell-reconstituted Rag1−/− hosts. The results show that Cobra1-overexpressing Tg CD8+ had a stronger antitumor killing effect compared to WT CD8+ (FIGS. 10A-10B). Immunophenotyping results show that there were more effector memory (CD44+CD62L−) and fewer naïve (CD44-CD62L+) CD8+ T cells in the Rag1 hosts reconstituted with Tg CD8+ compared to WT CD8+ (FIGS. 11A-11B).

Example 5

The Effect of Cobra1 T Cell Expression on Generation of Central Memory CD8+ T Cells Wild-type (CD45.1) and Cobra1 knockout (CD45.2) or wildtype (CD45.1) and Tg (Cobra1 overexpression) (CD45.2) CD8+ T cells were mixed at a ratio of 50:50 and intravenously transferred into B16 melanoma tumor-bearing Rag1 immunodeficient mice (FIG. 12A).

Flow cytometry shows that Cobra1 KO CD8+ T cells made up about 33% of the total tumor-infiltrating CD8+ cells in tumor bearing mice administered both wild-type and Cobra KO CD8+ T cells at 17 days post-transfer (FIG. 12B). T-CKO cells were not detectable 23 days post-transfer (FIG. 12C). In contrast, Tg CD8+ T cells made up about 75% of the total tumor-infiltrating CD8+ cells in tumor bearing mice administering both wild-type and Tg CD8+ T cells days post-transfer (FIGS. 12E & 12G). Tg CD8+ T cells made up about 90% of total tumor infiltrating CD8+ T cells at 23 days post-transfer (FIG.

To examine how Cobra1 expression affects T cell memory response, heat inactivated B16 melanoma tumor cells were injected subcutaneously to vaccinate wildtype and T-cell specific Cobra1 knockout mice (T-CKO). After two weeks, live B16 tumor cells were injected subcutaneously into the vaccinated mice and tumor curves were measured. Immunized wildtype mice had significantly smaller tumors compared to non-immunized wildtype mice and immunized or non-immunized T-CKO mice (FIG. 13A).

At the end of tumor growth, tumor infiltrating lymphocytes and tumor draining lymph nodes were analyzed by flow cytometry. Immunized wildtype mice generated about three times more central memory CD8+ T cells compared to non-immunized wildtype mice (FIG. 13B). Immunized T-CKO mice only had a slight increase in the number of effector memory CD8+ T cells compared to non-immunized T-CKO mice (FIG. 13C). Likewise, immunized wildtype mice had a large reduction in tumor volume at 15 days after challenge compared to non-immunized mice, while immunized T-CKO mice had a slight reduction in tumor volume compared to non-immunized T-CKO mice.

Thus, vaccination boosts central memory CD8+ T cells in tumor draining lymph nodes and effector memory CD8+ T cells in the tumor infiltrating population in wildtype but not T-cell specific Cobra 1 knockout mice. The data suggest that Cobra1 is required for memory response generated by heat-inactivated tumor cell vaccination.

Figure 14B:
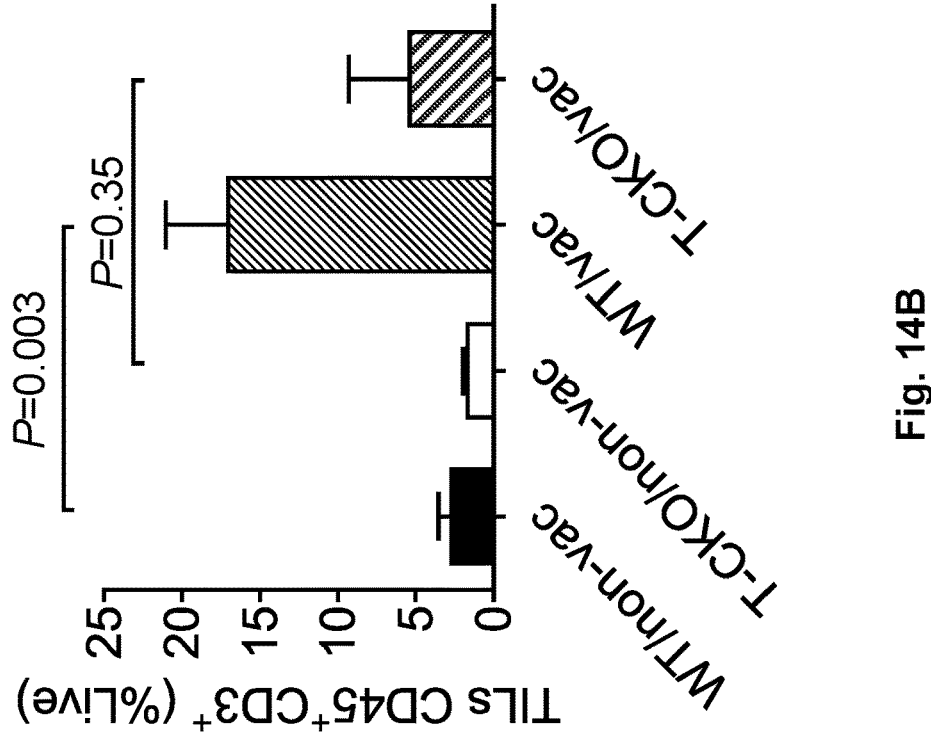
Figure 14A:
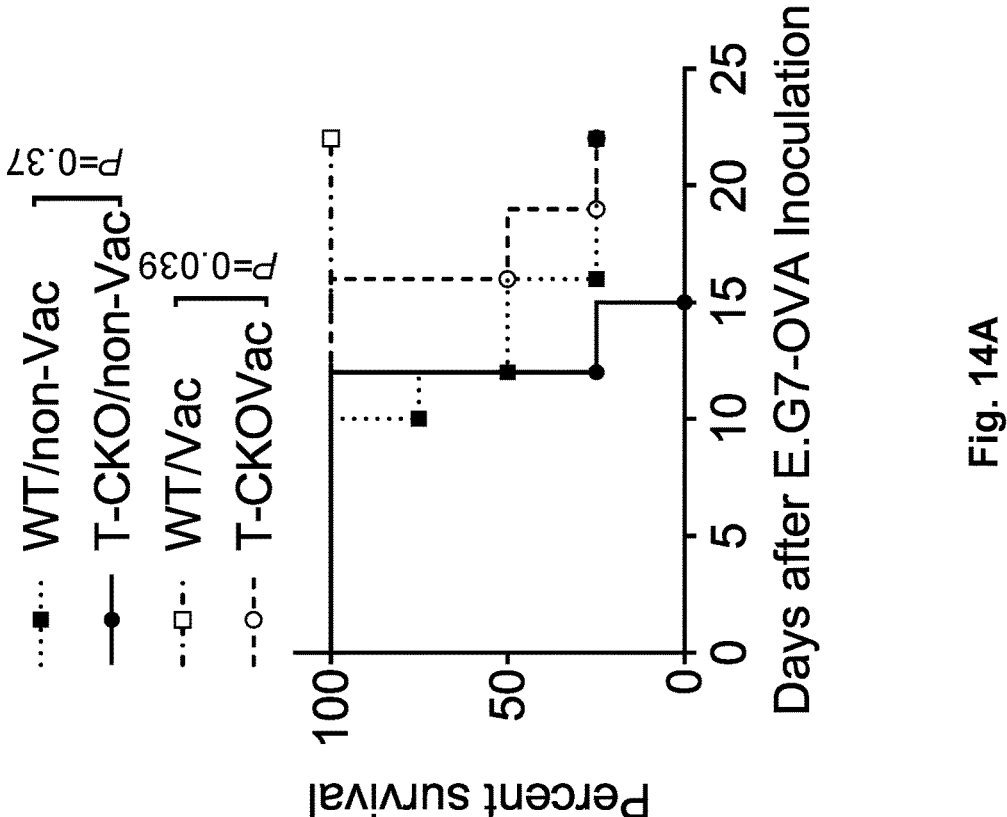
Figure 14D:
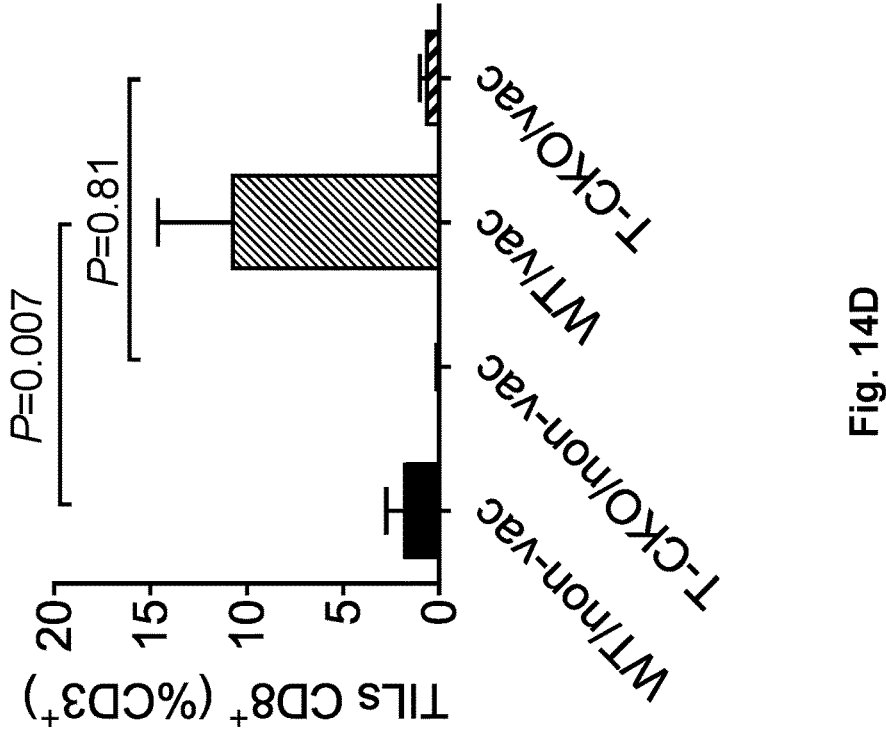
Figure 14C:
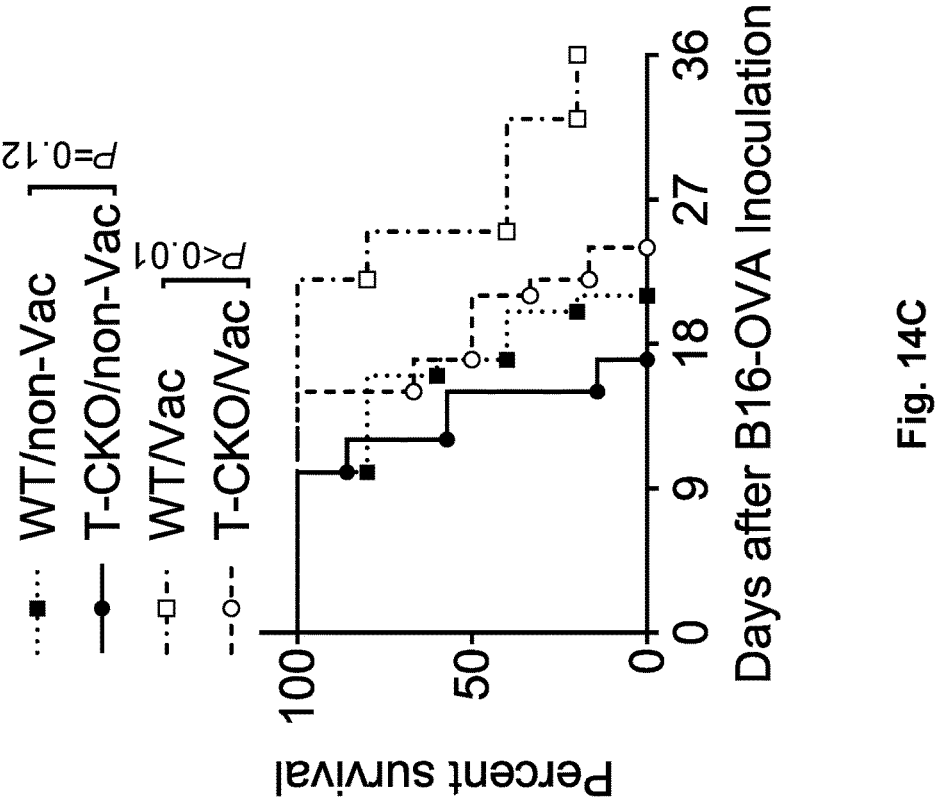

Next, ovalbumin (OVA) protein emulsified with Complete Freund's Adjuvant (CFA) was injected subcutaneously into WT and T-CKO mice for vaccination. Two weeks later, OVA emulsified with Incomplete Freund's Adjuvant (IFA) was injected subcutaneously to the same mice as a booster for vaccination. After another two weeks, E.G7-OVA lymphoma cells or B16-OVA melanoma cells were injected subcutaneously into the vaccinated mice. Survival of the tumor-bearing mice was examined (FIGS. 14A&14C). Vaccinated wildtype mice survived the longest compared to non-vaccinated wildtype and vaccinated and non-vaccinated T-CKO mice. Results show that vaccination boosts total tumor infiltrating CD3+ and CD8+ cells, in wildtype, but not knockout mice (FIGS. 14B&14D). The data suggest that Cobra1 is required for memory response generated by Ovalbumin vaccination.

CD8+ cells were isolated from parental wildtype and Tg (Cobra1 overexpression) mice and then intravenously transferred into Rag1 immunodeficient mice. E0071 tumor cells were then orthotopically inoculated into the mammary fat pad of Rag1 KO mice reconstituted with wildtype or Tg CD8+ T cells. Immunophenotyping analysis shows that Tg CD8+ receiving mice have a higher percentage of CD45+ total immune cells and CD8+ T cells in the tumor infiltrating population (FIGS. 15A&B). Notably, there are more effector memory (CD44+CD62L−), proliferating (Ki67+), IFNγ+, TNFα+ and polyfunctional (IFNγ+TNFα+) but less exhausted (PD1+Tim3+Lag3+) CD8+ cells from tumors grew in Tg versus wildtype CD8+ receiving mice (FIGS. 15C-15H).

Example 6

The Effect of T Cell Specific Cobra1 Expression on Car-T Efficacy

A bicistronic vector construct consisting of both human COBRA1 transgene and CD19-CAR will be introduced into primary healthy human T cells by using a retroviral system. The modified COBRA1 transgenic CAR-T cells will be tested in vitro in a tumor killing-based cytolysis assay and cytokine (IFNγ, TNFα, IL2, Granzyme B, perforin)-production assay. In addition, the COBRA1 transgenic CAR-T cells will be tested in vivo using xenograft tumor models. Briefly, Nalm6 human leukemia cell line will be intravenously inoculated into immunodeficient NSG mice. After tumor challenge, human COBRA1-overexpressing CAR T cells or control CAR T cells will be intravenously injected into tumor-bearing mice. Leukemia progression will be monitored by an in vivo luminescent imaging system. This method can be adapted for any NELF complex gene by replacing COBRA1 with the NELF complex gene of interest (NELFA, NELFC, NELFD, or NELFE).

To test the role of the human Cobra1 transgene in boosting TILs adoptive cell transfer therapy efficacy, TILs will be isolated from fresh primary human breast tumor tissues and corresponding patient's tumor cells will be harvested and cultured ex vivo. The human COBRA1 transgene vector and the control vector will be introduced into the TILs using a retroviral system. Individual human-derived tumor cells will be expanded and implanted into inguinal mammary fat pad of female immunodeficient NSG mice. When implanted tumors become palpable, tumor-bearing mice will be divided into two groups: one group will receive control TILs and the other one will receive COBRA1-overexpressing TILs derived from the same patient. Tumor volumes will be measured by digital calipers and tumors will be examined by immunophenotyping to assess the cytokine secretion (IFNγ, TNFα, IL2, etc.) and cytotoxicity (Granzyme B, perforin, etc.) of TILs. This method can be adapted for any NELF complex gene by replacing COBRA1 with the NELF complex gene of interest (NELFA, NELFC, NELFD, or NELFE).

To generate COBRA1 transformed/transfected T cells, COBRA1-expressing or control retroviral vectors will be transfected into 293T cells together with an envelope-encoding plasmid using Lipofectamine 2000. After 2-3 days, viral supernatants will be collected and cell debris will be removed by centrifugation. Primary T cells will be collected from human donors and activated in vitro using anti-CD3/CD28 antibodies and cultured in IL-2-containing medium. After 2-3 days of activation, T cells will be resuspended in viral supernatant and spin-infection will be carried out. Cells are then washed with cold PBS+5% FCS 2-3 times. Engineered cells are ready for in vitro or in vivo assessment. This method can be adapted for any NELF complex gene by replacing COBRA1 with the NELF complex gene of interest (NELFA, NELFC, NELFD, or NELFE).

What is claimed is:

1. A method of treating a cancer in a subject in need thereof, comprising: administering to the subject a therapeutically effective amount of a population of T cells modified to overexpress one or more subunits of the negative elongation factor (NELF) complex.

2. The method of claim 1, wherein the population of T cells are T lymphocytes or cytotoxic T lymphocytes.

3. The method of claim 1, wherein the population of T cells comprise autologous cells or allogeneic cells.

4. The method of claim 1, wherein the cancer comprises lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, or adenocarcinoma of the gastroesophageal junction.

5. The method of claim 1, wherein the population of T cells modified to overexpress one or more subunits of the NELF complex comprises CD3+ T cells, CD8+ T cells, CD4+ T cells, natural killer (NK) T cells, gamma delta T cells, a combination of CD4+ and CD8 T+ cells, memory T cells, cytokine-induced killer cells, or any combination thereof.

6. The method of claim 1, wherein the one or more subunits of the NELF complex comprise NELF-A, NELF-B, NELF-C, NELF-D, or NELF-E.

7. The method of claim 1,
wherein the subunit is NELF-A and comprises a sequence having at least 90% identity to the sequence set forth in SEQ ID NO:4;
wherein the subunit is NELF-B and comprises a sequence having at least 90% identity to the sequence set forth in SEQ ID NO:2;
wherein the subunit is NELF-C and comprises a sequence having at least 90% identity to the sequence set forth in SEQ ID NO:6;
wherein the subunit is NELF-D and comprises a sequence having at least 90% identity to the sequence set forth in SEQ ID NO:8; or wherein the subunit is NELF-E and comprises a sequence having at least 90% identity to the sequence set forth in SEQ ID NO:10.

8. The method of claim 1, wherein the overexpression of the one or more subunits of the NELF complex is at least 1.5 times, at least 2 times, at least 3 times, at least 5 times, or at least 10 times more than the endogenous expression level of the one or more subunits of the NELF complex.

9. The method of claim 1, wherein the T cells further express a chimeric antigen receptor (CAR).

10. The method of claim 6, wherein the CAR is specific for a tumor antigen.

11. The method of claim 10, wherein the tumor antigen is CD19, CD20, CD22, RORI, GD2, EBV protein or antigen, folate receptor, Mesothelin, human carcinoembryonic antigen, CD33/IL3Ra, c-Met, PSMA, Glycolipid F77, EGFRVIII, NY-ESO-1, MAGE-A3, MART-I, GP1000, or p53.

12. The method of claim 11, wherein the subunit of the NELF complex is NELF-B and wherein the tumor antigen is CD19.

13. The method of claim 1, further comprising preparing the population of T cells modified to overexpress one or more subunits of the NELF complex.

14. The method of claim 13, wherein preparing the population of T cells modified to overexpress one or more subunits of the NELF complex comprises isolating naïve T cells from the subject's resected tumor or tumors or by leukapheresis of the subject's blood.

15. The method of claim 14, further comprising introducing to the subject's isolated naïve T cells a nucleic acid sequence encoding the one or more subunits of the NELF complex.

16. The method of claim 15, wherein introducing the nucleic acid sequence encoding the one or more subunits of the NELF complex comprises using a viral vector.

17. The method of claim 16, wherein the viral vector is a lentiviral vector.

18. The method of claim 15,
wherein the subunit is NELF-A and comprises the sequence set forth in SEQ ID NO:3;
wherein the subunit is NELF-B and comprises the sequence set forth in SEQ ID NO:1;
wherein the subunit is NELF-C and comprises the sequence set forth in SEQ ID NO:5;
wherein the subunit is NELF-D and comprises the sequence set forth in SEQ ID NO:7; or
wherein the subunit is NELF-E and comprises the sequence set forth in SEQ ID NO:9.

19. The method of claim 1, wherein the population of T cells modified to overexpress one or more subunits of the NELF complex enhances the subject's T cell immune response to the cancer.

* * * * *

SEQUENCE LISTING

<160> NUMBER OF SEQ ID NOS: 10

<210> SEQ ID NO 1
<211> LENGTH: 1887
<212> TYPE: DNA
<213> ORGANISM: Artificial Sequence
<220> FEATURE:
<223> OTHER INFORMATION: COBRA1 nucleic acid sequence

<400> SEQUENCE: 1
ctggccgagc tggagggcgc cggggagcgg ggctcgggcg gtccccgagg cccggcggag      60

-continued

```
cgggcttctg gggtgtctgc ggcggcgccg ggggaacggg ctggggatgg ggcgcctagc        120
cgggcggtgg ccgggcctc ggccatgttc gcggggctgc aggacctggg cgtggccaac         180
ggcgaggacc tgaaggagac cctgaccaac tgcacggagc cgctcaaggc catcgagcag        240
ttccagacag agaatggtgt gctgctgcca tctcttcagt cagccctccc cttcttggac        300
ctgcacggga cgccgcggct ggagttccac cagtcggtat tcgatgagct gcgggacaag        360
ctgctggagc gagtgtcagc catcgcttcg gaggggaagg ctgaggaaag gtacaagaag        420
ctggaagacc ttctggagaa gagctttttct ctggtgaaga tgccgtccct gcagcccgtg       480
gtgatgtgcg tcatgaagca cctgcccaag gttccggaga aaaaactgaa gctggttatg        540
gctgacaagg agctgtatcg agcctgcgcc gtggaggtga agcggcagat ctggcaagac        600
aaccaggccc tcttcgggga cgaggtttcc ccactcctga agcagtacat cctggagaag        660
gagagcgctc tcttcagtac agagctctct gtcctgcaca actttttcag tccttcccc         720 aagaccaggc gccagggcga ggtggtgcag cggctgacgc ggatggtggg gaagaacgtg        780
aagctgtacg acatggtgct gcagtttctg cgcacgctct tcctgcgcac gcggaatgtg        840
cactactgca cgctgcgggc tgagctgctc atgtccctgc acgacctgga cgtgggtgaa        900
atctgcaccg tggacccgtg ccacaagttc acctggtgcc tggacgcctg catccgagag        960
cggttcgtgg acagcaagag ggcgcgggag ctgcaggggt ttctcgatgg cgtcaagaag       1020
ggccaggagc aggtgctggg ggacctgtcc atgatcctgt gtgaccccctt cgccatcaac      1080 acgctggcac tgagcacagt caggcacctg caggagctgg tcggccagga gacactgccc       1140
agggacagcc ccgacctcct gctgctgctc cggctgctgg cgctgggcca gggagcctgg       1200
gacatgatcg acagccaggt cttcaaggag cccaagatgg aggtagagct catcaccagg       1260
ttcctcccga tgctcatgtc cttcctggtg gatgactaca ctttcaatgt ggatcagaaa       1320
cttccggctg aggagaaagc cccagtctca tatccaaaca cacttcccga aagcttcact       1380
aagtttctgc aggagcagcg catggcctgc gaggtggggc tgtactacgt cctgcacatc       1440
accaagcaga ggaacaagaa cgcgctcctc cgcctgctgc ccgggctggt ggagaccttt       1500
ggcgacttgg cctttggcga catcttcctc cacctgctca cgggcaacct tgcgctgctg       1560
gccgacgaat ttgcccttga ggacttctgc agcagcctct tcgatggctt cttcctcacc       1620
gcctctccaa ggaaggagaa cgtgcaccgg cacgcgctgc ggctcctcat tcacctgcac       1680
cccagggtgg ccccgtctaa gctggaggcg ttgcagaagg ccctggagcc tacaggccag       1740
agcggagagg cagtgaagga gctttactcc cagctcggcg agaagctgga acagctggat       1800
caccggaagc ccagcccggc acaggctgcg gagacgccgg ccctggagct gccccctcccc       1860 agcgtgcccg ccccctgcccc gctctga                                         1887
```

<210> SEQ ID NO 2
<211> LENGTH: 628
<212> TYPE: PRT
<213> ORGANISM: Artificial Sequence
<220> FEATURE:
<223> OTHER INFORMATION: COBRA1 amino acid sequence

<400> SEQUENCE: 2

```
Met Ala Glu Leu Glu Gly Ala Gly Glu Arg Gly Ser Gly Gly Pro Arg
1               5                   10                  15

Gly Pro Ala Glu Arg Ala Ser Gly Val Ser Ala Ala Ala Pro Gly Glu
            20                  25                  30

Arg Ala Gly Asp Gly Ala Pro Ser Arg Ala Val Ala Gly Ala Ser Ala
```

```
              35                    40                    45

Met Phe Ala Gly Leu Gln Asp Leu Gly Val Ala Asn Gly Glu Asp Leu
         50                    55                    60

Lys Glu Thr Leu Thr Asn Cys Thr Glu Pro Leu Lys Ala Ile Glu Gln
65                     70                    75                    80

Phe Gln Thr Glu Asn Gly Val Leu Leu Pro Ser Leu Gln Ser Ala Leu
                   85                    90                    95

Pro Phe Leu Asp Leu His Gly Thr Pro Arg Leu Glu Phe His Gln Ser
              100                   105                   110

Val Phe Asp Glu Leu Arg Asp Lys Leu Leu Glu Arg Val Ser Ala Ile
              115                   120                   125

Ala Ser Glu Gly Lys Ala Glu Glu Arg Tyr Lys Lys Leu Glu Asp Leu
         130                   135                   140

Leu Glu Lys Ser Phe Ser Leu Val Lys Met Pro Ser Leu Gln Pro Val
145                   150                   155                   160

Val Met Cys Val Met Lys His Leu Pro Lys Val Pro Glu Lys Lys Leu
              165                   170                   175

Lys Leu Val Met Ala Asp Lys Glu Leu Tyr Arg Ala Cys Ala Val Glu
              180                   185                   190

Val Lys Arg Gln Ile Trp Gln Asp Asn Gln Ala Leu Phe Gly Asp Glu
         195                   200                   205

Val Ser Pro Leu Leu Lys Gln Tyr Ile Leu Glu Lys Glu Ser Ala Leu
         210                   215                   220

Phe Ser Thr Glu Leu Ser Val Leu His Asn Phe Phe Ser Pro Ser Pro
225                   230                   235                   240

Lys Thr Arg Arg Gln Gly Glu Val Val Gln Arg Leu Thr Arg Met Val
              245                   250                   255

Gly Lys Asn Val Lys Leu Tyr Asp Met Val Leu Gln Phe Leu Arg Thr
              260                   265                   270

Leu Phe Leu Arg Thr Arg Asn Val His Tyr Cys Thr Leu Arg Ala Glu
         275                   280                   285

Leu Leu Met Ser Leu His Asp Leu Asp Val Gly Glu Ile Cys Thr Val
         290                   295                   300

Asp Pro Cys His Lys Phe Thr Trp Cys Leu Asp Ala Cys Ile Arg Glu
305                   310                   315                   320

Arg Phe Val Asp Ser Lys Arg Ala Arg Glu Leu Gln Gly Phe Leu Asp
              325                   330                   335

Gly Val Lys Lys Gly Gln Glu Gln Val Leu Gly Asp Leu Ser Met Ile
              340                   345                   350

Leu Cys Asp Pro Phe Ala Ile Asn Thr Leu Ala Leu Ser Thr Val Arg
         355                   360                   365

His Leu Gln Glu Leu Val Gly Gln Glu Thr Leu Pro Arg Asp Ser Pro
         370                   375                   380

Asp Leu Leu Leu Leu Leu Arg Leu Leu Ala Leu Gly Gln Gly Ala Trp
385                   390                   395                   400

Asp Met Ile Asp Ser Gln Val Phe Lys Glu Pro Lys Met Glu Val Glu
              405                   410                   415

Leu Ile Thr Arg Phe Leu Pro Met Leu Met Ser Phe Leu Val Asp Asp
              420                   425                   430

Tyr Thr Phe Asn Val Asp Gln Lys Leu Pro Ala Glu Glu Lys Ala Pro
         435                   440                   445

Val Ser Tyr Pro Asn Thr Leu Pro Glu Ser Phe Thr Lys Phe Leu Gln
         450                   455                   460
```

```
Glu Gln Arg Met Ala Cys Glu Val Gly Leu Tyr Tyr Val Leu His Ile
465                 470                 475                 480

Thr Lys Gln Arg Asn Lys Asn Ala Leu Leu Arg Leu Leu Pro Gly Leu
                485                 490                 495

Val Glu Thr Phe Gly Asp Leu Ala Phe Gly Asp Ile Phe Leu His Leu
            500                 505                 510

Leu Thr Gly Asn Leu Ala Leu Leu Ala Asp Glu Phe Ala Leu Glu Asp
        515                 520                 525

Phe Cys Ser Ser Leu Phe Asp Gly Phe Phe Leu Thr Ala Ser Pro Arg
    530                 535                 540

Lys Glu Asn Val His Arg His Ala Leu Arg Leu Leu Ile His Leu His
545                 550                 555                 560

Pro Arg Val Ala Pro Ser Lys Leu Glu Ala Leu Gln Lys Ala Leu Glu
                565                 570                 575

Pro Thr Gly Gln Ser Gly Glu Ala Val Lys Glu Leu Tyr Ser Gln Leu
            580                 585                 590

Gly Glu Lys Leu Glu Gln Leu Asp His Arg Lys Pro Ser Pro Ala Gln
        595                 600                 605

Ala Ala Glu Thr Pro Ala Leu Glu Leu Pro Leu Pro Ser Val Pro Ala
    610                 615                 620

Pro Ala Pro Leu
625

<210> SEQ ID NO 3
<211> LENGTH: 1587
<212> TYPE: DNA
<213> ORGANISM: Artificial Sequence
<220> FEATURE:
<223> OTHER INFORMATION: (NELFA nucleic acid sequence)

<400> SEQUENCE: 3
atggcgtcca tgcgggagag cgacacgggc ctgtggctgc acaacaagct gggggccacg      60
gacgagctgt gggcgccgcc cagcatcgcg tccctgctca cggccgcggt catcgacaac     120
atccgtctct gcttccatgg cctctcgtcg gcagtgaagc tcaagttgct actcgggacg     180
ctgcacctcc cgcgccgcac ggtggacgag atgaagggcg ccctaatgga gatcatccag     240
ctcgccagcc tcgactcgga cccctgggtg ctcatggtcg ccgacatctt gaagtccttt     300
ccggacacag gctcgcttaa cctggagctg gaggagcaga tcccaacgt tcaggatatt     360 ttgggagaac ttagagaaaa ggtgggtgag tgtgaagcgt ctgccatgct gccactggag     420
tgccagtact tgaacaaaaa cgccctgacg accctcgcgg gaccgctcac tcccccggtg     480
aagcattttc agttaaagcg gaaacccaag agcgccacgc tgcgggcgga gctgctgcag     540
aagtccacgg agaccgccca gcagttgaag cggagcgccg gggtgcccct tccacgccaag     600 ggccggggggc tgctgcggaa gatggacacc accaccccac tcaaaggcat cccgaagcag     660
gcgcccttca gaagccccac ggcgcccagc gtcttcagcc ccacagggaa ccggacccc      720 atcccgcctt ccaggacgct gctgcggaag aacgaggtg tgaagctgct ggacatctct     780
gagctggata tggttggcgc tggccgagag gcgaagcgga gaaggaagac tctcgatgcg     840
gaggtggtgg agaagccggc caaggaggaa acggtggtgg agaacgccac cccggactac     900
gcagccggcc tggtgtccac gcagaaactt gggtccctga caatgagcc tgcgctgccc     960 tccacgagct accttccctc cacgcccagc gtggttcccg cctcctccta catcccagc    1020 tccgagacgc ccccagcccc atcttcccgg gaagccagcc gcccaccaga ggagcccagc    1080
```

```
gccccgagcc ccacgttgcc agcgcagttc aagcagcggg cgcccatgta caacagcggc       1140
ctgagccctg ccacacccac gcctgcggcg cccacctcgc ctctgacacc caccacacct       1200
ccggctgtcg cccctaccac tcagacaccc ccggttgcca tggtggcccc gcagacccag       1260
gcccctgctc agcagcagcc taagaagaac ctgtccctca cgagagagca gatgttcgct       1320
gcccaggaga tgttcaagac ggccaacaaa gtcacgcggc ccgagaaggc cctcatcctg       1380
ggcttcatgg ccggctcccg agagaacccg tgccaggagc agggggacgt gatccagatc       1440
aagctgagcg agcacacgga ggacctgccc aaggcggacg gccagggtag cacaaccatg       1500
ctggtggaca cagtgtttga gatgaactat gccacgggcc agtggacgcg cttcaagaag       1560
tacaagccca tgaccaatgt gtcctag                                          1587
```

<210> SEQ ID NO 4
<211> LENGTH: 528
<212> TYPE: PRT
<213> ORGANISM: Artificial Sequence
<220> FEATURE:
<223> OTHER INFORMATION: NELFA amino acid sequence

<400> SEQUENCE: 4

```
Met Ala Ser Met Arg Glu Ser Asp Thr Gly Leu Trp Leu His Asn Lys
1               5                   10                  15

Leu Gly Ala Thr Asp Glu Leu Trp Ala Pro Pro Ser Ile Ala Ser Leu
            20                  25                  30

Leu Thr Ala Ala Val Ile Asp Asn Ile Arg Leu Cys Phe His Gly Leu
        35                  40                  45

Ser Ser Ala Val Lys Leu Lys Leu Leu Leu Gly Thr Leu His Leu Pro
    50                  55                  60

Arg Arg Thr Val Asp Glu Met Lys Gly Ala Leu Met Glu Ile Ile Gln
65                  70                  75                  80

Leu Ala Ser Leu Asp Ser Asp Pro Trp Val Leu Met Val Ala Asp Ile
                85                  90                  95

Leu Lys Ser Phe Pro Asp Thr Gly Ser Leu Asn Leu Glu Leu Glu Glu
            100                 105                 110

Gln Asn Pro Asn Val Gln Asp Ile Leu Gly Glu Leu Arg Glu Lys Val
        115                 120                 125

Gly Glu Cys Glu Ala Ser Ala Met Leu Pro Leu Glu Cys Gln Tyr Leu
    130                 135                 140

Asn Lys Asn Ala Leu Thr Thr Leu Ala Gly Pro Leu Thr Pro Pro Val
145                 150                 155                 160

Lys His Phe Gln Leu Lys Arg Lys Pro Lys Ser Ala Thr Leu Arg Ala
                165                 170                 175

Glu Leu Leu Gln Lys Ser Thr Glu Thr Ala Gln Gln Leu Lys Arg Ser
            180                 185                 190

Ala Gly Val Pro Phe His Ala Lys Gly Arg Gly Leu Leu Arg Lys Met
        195                 200                 205

Asp Thr Thr Thr Pro Leu Lys Gly Ile Pro Lys Gln Ala Pro Phe Arg
    210                 215                 220

Ser Pro Thr Ala Pro Ser Val Phe Ser Pro Thr Gly Asn Arg Thr Pro
225                 230                 235                 240

Ile Pro Pro Ser Arg Thr Leu Leu Arg Lys Glu Arg Gly Val Lys Leu
                245                 250                 255

Leu Asp Ile Ser Glu Leu Asp Met Val Gly Ala Gly Arg Glu Ala Lys
            260                 265                 270
```

```
Arg Arg Arg Lys Thr Leu Asp Ala Glu Val Val Glu Lys Pro Ala Lys
        275                 280                 285

Glu Glu Thr Val Val Glu Asn Ala Thr Pro Asp Tyr Ala Ala Gly Leu
    290                 295                 300

Val Ser Thr Gln Lys Leu Gly Ser Leu Asn Asn Glu Pro Ala Leu Pro
305                 310                 315                 320

Ser Thr Ser Tyr Leu Pro Ser Thr Pro Ser Val Val Pro Ala Ser Ser
                325                 330                 335

Tyr Ile Pro Ser Ser Glu Thr Pro Pro Ala Pro Ser Ser Arg Glu Ala
                340                 345                 350

Ser Arg Pro Pro Glu Glu Pro Ser Ala Pro Ser Pro Thr Leu Pro Ala
        355                 360                 365

Gln Phe Lys Gln Arg Ala Pro Met Tyr Asn Ser Gly Leu Ser Pro Ala
    370                 375                 380

Thr Pro Thr Pro Ala Ala Pro Thr Ser Pro Leu Thr Pro Thr Thr Pro
385                 390                 395                 400

Pro Ala Val Ala Pro Thr Thr Gln Thr Pro Pro Val Ala Met Val Ala
                405                 410                 415

Pro Gln Thr Gln Ala Pro Ala Gln Gln Gln Pro Lys Lys Asn Leu Ser
                420                 425                 430

Leu Thr Arg Glu Gln Met Phe Ala Ala Gln Glu Met Phe Lys Thr Ala
        435                 440                 445

Asn Lys Val Thr Arg Pro Glu Lys Ala Leu Ile Leu Gly Phe Met Ala
    450                 455                 460

Gly Ser Arg Glu Asn Pro Cys Gln Glu Gln Gly Asp Val Ile Gln Ile
465                 470                 475                 480

Lys Leu Ser Glu His Thr Glu Asp Leu Pro Lys Ala Asp Gly Gln Gly
                485                 490                 495

Ser Thr Thr Met Leu Val Asp Thr Val Phe Glu Met Asn Tyr Ala Thr
                500                 505                 510

Gly Gln Trp Thr Arg Phe Lys Lys Tyr Lys Pro Met Thr Asn Val Ser
        515                 520                 525
```

```
<210> SEQ ID NO 5
<211> LENGTH: 1773
<212> TYPE: DNA
<213> ORGANISM: Artificial Sequence
<220> FEATURE:
<223> OTHER INFORMATION: (NELFC nucleic acid sequence)

<400> SEQUENCE: 5
atggcggggg ccgtgccggg cgccatcatg gacgaggact actacgggag cgcggccgag      60
tggggcgacg aggctgacgg cggccagcag gaggatgatt ctggagaagg agaggatgat     120
gcggaggttc agcaagaatg cctgcataaa ttttccaccc gggattatat catggaaccc     180
tccatcttca acactctgaa gaggtatttt caggcaggag ggtctccaga gaatgttatc     240
cagctcttat ctgaaaacta caccgctgtg gcccagactg tgaacctgct ggccgagtgg     300
ctcattcaga caggtgttga gccagtgcag gttcaggaaa ctgtggaaaa tcacttgaag     360
agtttgctga tcaaacattt tgaccccccgc aaagcagatt ctatttttac tgaagaagga     420
gagaccccag cgtggctgga acagatgatt gcacatacca cgtggcggga cctttttttat     480 aaactggctg aagcccatcc agactgtttg atgctgaact tcaccgttaa gcttatttct     540
gacgcagggt accagggggga gatcaccagt gtgtccacag catgccagca gctagaagtg     600
```

-continued

```
ttctcgagag tgctccggac ctctctagct acaatttttag atggaggaga agaaaacctt    660
gaaaaaaatc tccctgagtt tgccaagatg gtgtgccacg gggagcacac gtacctgttt    720
gcccaggcca tgatgtccgt gctggcccag gaggagcagg ggggctccgc tgtgcgcagg    780
atcgcccagg aagtgcagcg ctttgcccag gagaaaggtc atgacgccag tcagatcaca    840
ctagccttgg gcacagctgc ctcctacccc agggcctgcc aggctctcgg ggccatgctg    900
tccaaaggag ccctgaaccc tgctgacatc accgtcctgt tcaagatgtt cacaagcatg    960
gaccctcctc cggttgaact tatccgcgtt ccagccttcc tggacctgtt catgcagtca   1020
ctctttaaac caggggctcg gatcaaccag gaccacaagc acaaatacat ccacatcttg   1080
gcgtacgcag caagcgtggt tgagacctgg aagaagaaca agcgagtgag catcaataaa   1140
gatgagctga gtcaacgtc aaaagctgtc gaaaccgttc acaatttgtg ttgcaacgag   1200
aacaaagggg cctctgaact agtggcagaa ttgagcacac tttatcagtg tattaggttt   1260
ccagtggtag caatgggtgt gctgaagtgg gtggattgga ctgtatcaga accaaggtac   1320
tttcagctgc agactgacca tacccctgtc cacctggcgt tgctggatga gatcagcacc   1380
tgccaccagc tcctgcaccc ccaggtcctg cagctgcttg ttaagctttt tgagactgag   1440
cactcccagc tggacgtgat gggagcagct gagttgaaga agacactgct ggacaggatg   1500
gttcacctgc tgagtcgagg ttatgtactt cctgttgtca gttacatccg aaagtgtctg   1560
gagaagctgg acactgacat ttcactcatt cgctattttg tcactgaggt gctggacgtc   1620
attgctcctc cttatacctc tgacttcgtg caactttttcc tccccatcct ggagaatgac   1680
agcatcgcag gtaccatcaa aacggaaggc gagcatgacc ctgtgacgga gtttatagct   1740
cactgcaaat ctaacttcat catggtgaac taa                                 1773
```

```
<210> SEQ ID NO 6
<211> LENGTH: 590
<212> TYPE: PRT
<213> ORGANISM: Artificial Sequence
<220> FEATURE:
<223> OTHER INFORMATION: NELFC amino acid sequence

<400> SEQUENCE: 6

Met Ala Gly Ala Val Pro Gly Ala Ile Met Asp Glu Asp Tyr Tyr Gly
1               5                   10                  15

Ser Ala Ala Glu Trp Gly Asp Glu Ala Asp Gly Gly Gln Gln Glu Asp
            20                  25                  30

Asp Ser Gly Glu Gly Glu Asp Asp Ala Glu Val Gln Gln Glu Cys Leu
        35                  40                  45

His Lys Phe Ser Thr Arg Asp Tyr Ile Met Glu Pro Ser Ile Phe Asn
    50                  55                  60

Thr Leu Lys Arg Tyr Phe Gln Ala Gly Gly Ser Pro Glu Asn Val Ile
65                  70                  75                  80

Gln Leu Leu Ser Glu Asn Tyr Thr Ala Val Ala Gln Thr Val Asn Leu
                85                  90                  95

Leu Ala Glu Trp Leu Ile Gln Thr Gly Val Glu Pro Val Gln Val Gln
            100                 105                 110

Glu Thr Val Glu Asn His Leu Lys Ser Leu Leu Ile Lys His Phe Asp
        115                 120                 125

Pro Arg Lys Ala Asp Ser Ile Phe Thr Glu Glu Gly Glu Thr Pro Ala
    130                 135                 140

Trp Leu Glu Gln Met Ile Ala His Thr Thr Trp Arg Asp Leu Phe Tyr
145                 150                 155                 160
```

-continued

```
Lys Leu Ala Glu Ala His Pro Asp Cys Leu Met Leu Asn Phe Thr Val
                165             170             175

Lys Leu Ile Ser Asp Ala Gly Tyr Gln Gly Glu Ile Thr Ser Val Ser
                180             185             190

Thr Ala Cys Gln Gln Leu Glu Val Phe Ser Arg Val Leu Arg Thr Ser
            195             200             205

Leu Ala Thr Ile Leu Asp Gly Gly Glu Glu Asn Leu Glu Lys Asn Leu
        210             215             220

Pro Glu Phe Ala Lys Met Val Cys His Gly Glu His Thr Tyr Leu Phe
225             230             235             240

Ala Gln Ala Met Met Ser Val Leu Ala Gln Glu Glu Gln Gly Gly Ser
                245             250             255

Ala Val Arg Arg Ile Ala Gln Glu Val Gln Arg Phe Ala Gln Glu Lys
                260             265             270

Gly His Asp Ala Ser Gln Ile Thr Leu Ala Leu Gly Thr Ala Ala Ser
            275             280             285

Tyr Pro Arg Ala Cys Gln Ala Leu Gly Ala Met Leu Ser Lys Gly Ala
        290             295             300

Leu Asn Pro Ala Asp Ile Thr Val Leu Phe Lys Met Phe Thr Ser Met
305             310             315             320

Asp Pro Pro Pro Val Glu Leu Ile Arg Val Pro Ala Phe Leu Asp Leu
                325             330             335

Phe Met Gln Ser Leu Phe Lys Pro Gly Ala Arg Ile Asn Gln Asp His
                340             345             350

Lys His Lys Tyr Ile His Ile Leu Ala Tyr Ala Ala Ser Val Val Glu
            355             360             365

Thr Trp Lys Lys Asn Lys Arg Val Ser Ile Asn Lys Asp Glu Leu Lys
        370             375             380

Ser Thr Ser Lys Ala Val Glu Thr Val His Asn Leu Cys Cys Asn Glu
385             390             395             400

Asn Lys Gly Ala Ser Glu Leu Val Ala Glu Leu Ser Thr Leu Tyr Gln
                405             410             415

Cys Ile Arg Phe Pro Val Val Ala Met Gly Val Leu Lys Trp Val Asp
            420             425             430

Trp Thr Val Ser Glu Pro Arg Tyr Phe Gln Leu Gln Thr Asp His Thr
            435             440             445

Pro Val His Leu Ala Leu Leu Asp Glu Ile Ser Thr Cys His Gln Leu
        450             455             460

Leu His Pro Gln Val Leu Gln Leu Leu Val Lys Leu Phe Glu Thr Glu
465             470             475             480

His Ser Gln Leu Asp Val Met Glu Gln Leu Glu Leu Lys Lys Thr Leu
                485             490             495

Leu Asp Arg Met Val His Leu Leu Ser Arg Gly Tyr Val Leu Pro Val
                500             505             510

Val Ser Tyr Ile Arg Lys Cys Leu Glu Lys Leu Asp Thr Asp Ile Ser
            515             520             525

Leu Ile Arg Tyr Phe Val Thr Glu Val Leu Asp Val Ile Ala Pro Pro
        530             535             540

Tyr Thr Ser Asp Phe Val Gln Leu Phe Leu Pro Ile Leu Glu Asn Asp
545             550             555             560

Ser Ile Ala Gly Thr Ile Lys Thr Glu Gly Glu His Asp Pro Val Thr
                565             570             575
```

-continued

```
Glu Phe Ile Ala His Cys Lys Ser Asn Phe Ile Met Val Asn
        580                 585                 590
```

<210> SEQ ID NO 7
<211> LENGTH: 1746
<212> TYPE: DNA
<213> ORGANISM: Artificial Sequence
<220> FEATURE:
<223> OTHER INFORMATION: NELFD nucleic acid sequence

<400> SEQUENCE: 7

```
atggacgagg actactacgg gagcgcggcc gagtggggcg acgaggctga cggcggccag      60
caggaggatg attctggaga aggagaggat gatgcggagg ttcagcaaga atgcctgcat     120
aaattttcca cccgggatta tatcatggaa ccctccatct tcaacactct gaagaggtat     180
tttcaggcag gagggtctcc agagaatgtt atccagctct tatctgaaaa ctacaccgct     240
gtggcccaga ctgtgaacct gctggccgag tggctcattc agacaggtgt tgagccagtg     300
caggttcagg aaactgtgga aaatcacttg aagagtttgc tgatcaaaca ttttgacccc     360
cgcaaagcag attctatttt tactgaagaa ggagagaccc cagcgtggct ggaacagatg     420
attgcacata ccacgtggcg ggaccttttt tataaactgg ctgaagccca tccagactgt     480
ttgatgctga acttcaccgt taagcttatt tctgacgcag ggtaccaggg ggagatcacc     540
agtgtgtcca cagcatgcca gcagctagaa gtgttctcga gagtgctccg gacctctcta     600
gctacaattt tagatggagg agaagaaaac cttgaaaaaa atctccctga gtttgccaag     660
atggtgtgcc acggggagca cacgtacctg tttgcccagg ccatgatgtc cgtgctggcc     720
caggaggagc aggggggctc cgctgtgcgc aggatcgccc aggaagtgca gcgctttgcc     780
caggagaaag gtcatgacgc cagtcagatc acactagcct tgggcacagc tgcctcctac     840
cccagggcct gccaggctct cggggccatg ctgtccaaag agccctgaa ccctgctgac      900 atcaccgtcc tgttcaagat gttcacaagc atggaccctc ctccggttga acttatccgc     960
gttccagcct cctggacct gttcatgcag tcactcttta aaccagggggc tcggatcaac    1020 caggaccaca agcacaaata catccacatc ttggcgtacg cagcaagcgt ggttgagacc    1080
tggaagaaga acaagcgagt gagcatcaat aaagatgagc tgaagtcaac gtcaaaagct    1140
gtcgaaaccg ttcacaattt gtgttgcaac gagaacaaag gggcctctga actagtggca    1200
gaattgagca cactttatca gtgtattagg tttccagtgg tagcaatggg tgtgctgaag    1260
tgggtggatt ggactgtatc agaaccaagg tactttcagc tgcagactga ccataccct     1320 gtccacctgg cgttgctgga tgagatcagc acctgccacc agctcctgca cccccaggtc    1380
ctgcagctgc ttgttaagct ttttgagact gagcactccc agctggacgt gatggagcag    1440
cttgagttga agaagacact gctggacagg atggttcacc tgctgagtcg aggttatgta    1500
cttcctgttg tcagttacat ccgaaagtgt ctggagaagc tggacactga catttcactc    1560
attcgctatt ttgtcactga ggtgctggac gtcattgctc ctccttatac ctctgacttc    1620
gtgcaacttt tcctccccat cctggagaat gacagcatcg caggtaccat caaaacggaa    1680
ggcgagcatg accctgtgac ggagtttata gctcactgca aatctaactt catcatggtg    1740
aactaa                                                               1746
```

<210> SEQ ID NO 8
<211> LENGTH: 581
<212> TYPE: PRT
<213> ORGANISM: Artificial Sequence
<220> FEATURE:

-continued

```
<223> OTHER INFORMATION: NELFD amino acid sequence

<400> SEQUENCE: 8

Met Asp Glu Asp Tyr Tyr Gly Ser Ala Ala Glu Trp Gly Asp Glu Ala
1               5                   10                  15

Asp Gly Gly Gln Gln Glu Asp Asp Ser Gly Glu Gly Glu Asp Asp Ala
            20                  25                  30

Glu Val Gln Gln Glu Cys Leu His Lys Phe Ser Thr Arg Asp Tyr Ile
        35                  40                  45

Met Glu Pro Ser Ile Phe Asn Thr Leu Lys Arg Tyr Phe Gln Ala Gly
    50                  55                  60

Gly Ser Pro Glu Asn Val Ile Gln Leu Leu Ser Glu Asn Tyr Thr Ala
65                  70                  75                  80

Val Ala Gln Thr Val Asn Leu Leu Ala Glu Trp Leu Ile Gln Thr Gly
            85                  90                  95

Val Glu Pro Val Gln Val Gln Glu Thr Val Glu Asn His Leu Lys Ser
            100                 105                 110

Leu Leu Ile Lys His Phe Asp Pro Arg Lys Ala Asp Ser Ile Phe Thr
            115                 120                 125

Glu Glu Gly Glu Thr Pro Ala Trp Leu Glu Gln Met Ile Ala His Thr
    130                 135                 140

Thr Trp Arg Asp Leu Phe Tyr Lys Leu Ala Glu Ala His Pro Asp Cys
145                 150                 155                 160

Leu Met Leu Asn Phe Thr Val Lys Leu Ile Ser Asp Ala Gly Tyr Gln
                165                 170                 175

Gly Glu Ile Thr Ser Val Ser Thr Ala Cys Gln Gln Leu Glu Val Phe
            180                 185                 190

Ser Arg Val Leu Arg Thr Ser Leu Ala Thr Ile Leu Asp Gly Gly Glu
            195                 200                 205

Glu Asn Leu Glu Lys Asn Leu Pro Glu Phe Ala Lys Met Val Cys His
    210                 215                 220

Gly Glu His Thr Tyr Leu Phe Ala Gln Ala Met Met Ser Val Leu Ala
225                 230                 235                 240

Gln Glu Glu Gln Gly Gly Ser Ala Val Arg Arg Ile Ala Gln Glu Val
            245                 250                 255

Gln Arg Phe Ala Gln Glu Lys Gly His Asp Ala Ser Gln Ile Thr Leu
            260                 265                 270

Ala Leu Gly Thr Ala Ala Ser Tyr Pro Arg Ala Cys Gln Ala Leu Gly
            275                 280                 285

Ala Met Leu Ser Lys Gly Ala Leu Asn Pro Ala Asp Ile Thr Val Leu
    290                 295                 300

Phe Lys Met Phe Thr Ser Met Asp Pro Pro Val Glu Leu Ile Arg
305                 310                 315                 320

Val Pro Ala Phe Leu Asp Leu Phe Met Gln Ser Leu Phe Lys Pro Gly
            325                 330                 335

Ala Arg Ile Asn Gln Asp His Lys His Lys Tyr Ile His Ile Leu Ala
            340                 345                 350

Tyr Ala Ala Ser Val Val Glu Thr Trp Lys Lys Asn Lys Arg Val Ser
            355                 360                 365

Ile Asn Lys Asp Glu Leu Lys Ser Thr Ser Lys Ala Val Glu Thr Val
    370                 375                 380

His Asn Leu Cys Cys Asn Glu Asn Lys Gly Ala Ser Glu Leu Val Ala
385                 390                 395                 400
```

-continued

```
Glu Leu Ser Thr Leu Tyr Gln Cys Ile Arg Phe Pro Val Val Ala Met
            405                 410                 415

Gly Val Leu Lys Trp Val Asp Trp Thr Val Ser Glu Pro Arg Tyr Phe
            420                 425                 430

Gln Leu Gln Thr Asp His Thr Pro Val His Leu Ala Leu Leu Asp Glu
            435                 440                 445

Ile Ser Thr Cys His Gln Leu Leu His Pro Gln Val Leu Gln Leu Leu
    450                 455                 460

Val Lys Leu Phe Glu Thr Glu His Ser Gln Leu Asp Val Met Glu Gln
465                 470                 475                 480

Leu Glu Leu Lys Lys Thr Leu Leu Asp Arg Met Val His Leu Leu Ser
            485                 490                 495

Arg Gly Tyr Val Leu Pro Val Val Ser Tyr Ile Arg Lys Cys Leu Glu
            500                 505                 510

Lys Leu Asp Thr Asp Ile Ser Leu Ile Arg Tyr Phe Val Thr Glu Val
            515                 520                 525

Leu Asp Val Ile Ala Pro Pro Tyr Thr Ser Asp Phe Val Gln Leu Phe
    530                 535                 540

Leu Pro Ile Leu Glu Asn Asp Ser Ile Ala Gly Thr Ile Lys Thr Glu
545                 550                 555                 560

Gly Glu His Asp Pro Val Thr Glu Phe Ile Ala His Cys Lys Ser Asn
            565                 570                 575

Phe Ile Met Val Asn
            580
```

```
<210> SEQ ID NO 9
<211> LENGTH: 1143
<212> TYPE: DNA
<213> ORGANISM: Artificial Sequence
<220> FEATURE:
<223> OTHER INFORMATION: NELFE nucleic acid sequence

<400> SEQUENCE: 9
atgttggtga tacccccggg actgagcgag gaagaggagg ctctgcagaa gaaattcaac      60
aagctcaaga aaagaaaaa ggcattgctg gctctgaaga agcaaagtag cagcagcaca     120
accagccaag gtggtgtcaa acgctcacta tcagagcagc ctgtcatgga cacagccaca     180
gcaacagagc aggcaaagca gctggtgaag tcaggagcca tcagtgccat caaggctgag     240
accaagaact caggcttcaa gcgttctcga acccttgagg ggaagttaaa ggaccccgag     300
aagggaccag tccccacttt ccagccgttc cagaggagca tatctgctga tgatgacctg     360
caagagtcat ccagacgtcc ccagaggaaa tctctgtatg agagctttgt gtcttctagt     420
gatcgacttc gagaactagg accagatgga gaagaggcag agggcccagg ggctggtgat     480
ggtccccctc gaagctttga ctggggctat gaagaacgca gtggtgccca ctcctcagcc     540
tcccctcccc gaagccgcag ccgggaccgc agccatgaga ggaaccggga cagagaccga     600
gatcgggagc gggatcgaga ccgggatcga gacagagaca gagagcggga cagggatcgg     660
gatcgggatc gagatcgaga ccgggaacgg gacagggatc gggagcggga tcgagaccga     720
gaccgagagg gtcctttccg caggtcggat tcattccctg aacggcgagc ccctaggaaa     780
gggaatactc tctatgtata tggagaagac atgcacccca cccttctccg tggggccttc     840
tctccttttg aaacatcat tgacctctcc atggacccac ccagaaactg tgccttcgtc     900
acctatgaaa agatggagtc agcagatcag gccgttgctg agctcaacgg acccaggtg     960 gagtctgtac agctcaaagt caacatagcc cgaaaacagc ccatgctgga tgccgctact    1020
```

-continued

```
ggcaagtctg tctggggctc cctcgctgtc cagaacagcc ctaagggttg ccaccgggac    1080
aagaggaccc agattgtcta cagtgatgac gtctacaagg aaaaccttgt ggatggcttc    1140
tag                                                                  1143
```

<210> SEQ ID NO 10
<211> LENGTH: 380
<212> TYPE: PRT
<213> ORGANISM: Artificial Sequence
<220> FEATURE:
<223> OTHER INFORMATION: NELFE amino acid sequence

<400> SEQUENCE: 10

```
Met Leu Val Ile Pro Pro Gly Leu Ser Glu Glu Glu Glu Ala Leu Gln
1               5                   10                  15

Lys Lys Phe Asn Lys Leu Lys Lys Lys Lys Ala Leu Leu Ala Leu
                20                  25                  30

Lys Lys Gln Ser Ser Ser Ser Thr Thr Ser Gln Gly Gly Val Lys Arg
            35                  40                  45

Ser Leu Ser Glu Gln Pro Val Met Asp Thr Ala Thr Ala Thr Glu Gln
        50                  55                  60

Ala Lys Gln Leu Val Lys Ser Gly Ala Ile Ser Ala Ile Lys Ala Glu
65                  70                  75                  80

Thr Lys Asn Ser Gly Phe Lys Arg Ser Arg Thr Leu Glu Gly Lys Leu
                85                  90                  95

Lys Asp Pro Glu Lys Gly Pro Val Pro Thr Phe Gln Pro Phe Gln Arg
            100                 105                 110

Ser Ile Ser Ala Asp Asp Asp Leu Gln Glu Ser Ser Arg Arg Pro Gln
        115                 120                 125

Arg Lys Ser Leu Tyr Glu Ser Phe Val Ser Ser Ser Asp Arg Leu Arg
    130                 135                 140

Glu Leu Gly Pro Asp Gly Glu Glu Ala Glu Gly Pro Gly Ala Gly Asp
145                 150                 155                 160

Gly Pro Pro Arg Ser Phe Asp Trp Gly Tyr Glu Glu Arg Ser Gly Ala
                165                 170                 175

His Ser Ser Ala Ser Pro Pro Arg Ser Arg Ser Arg Asp Arg Ser His
            180                 185                 190

Glu Arg Asn Arg Asp Arg Asp Arg Asp Arg Glu Arg Asp Arg Asp Arg
        195                 200                 205

Asp Arg Asp Arg Asp Arg Glu Arg Asp Arg Asp Arg Asp Arg Asp Arg
    210                 215                 220

Asp Arg Asp Arg Glu Arg Asp Arg Asp Arg Glu Arg Asp Arg Asp Arg
225                 230                 235                 240

Asp Arg Glu Gly Pro Phe Arg Arg Ser Asp Ser Phe Pro Glu Arg Arg
                245                 250                 255

Ala Pro Arg Lys Gly Asn Thr Leu Tyr Val Tyr Gly Glu Asp Met Thr
            260                 265                 270

Pro Thr Leu Leu Arg Gly Ala Phe Ser Pro Phe Gly Asn Ile Ile Asp
        275                 280                 285

Leu Ser Met Asp Pro Pro Arg Asn Cys Ala Phe Val Thr Tyr Glu Lys
    290                 295                 300

Met Glu Ser Ala Asp Gln Ala Val Ala Glu Leu Asn Gly Thr Gln Val
305                 310                 315                 320

Glu Ser Val Gln Leu Lys Val Asn Ile Ala Arg Lys Gln Pro Met Leu
                325                 330                 335
```

-continued

```
Asp Ala Ala Thr Gly Lys Ser Val Trp Gly Ser Leu Ala Val Gln Asn
            340                 345                 350

Ser Pro Lys Gly Cys His Arg Asp Lys Arg Thr Gln Ile Val Tyr Ser
        355                 360                 365

Asp Asp Val Tyr Lys Glu Asn Leu Val Asp Gly Phe
    370                 375                 380
```